(12) United States Patent
Dang

(10) Patent No.: US 7,774,216 B2
(45) Date of Patent: Aug. 10, 2010

(54) COMPUTER-IMPLEMENTED METHOD FOR GROUPING MEDICAL CLAIMS BASED UPON CHANGES IN PATIENT CONDITION

(75) Inventor: Dennis K. Dang, Phoenix, AZ (US)

(73) Assignee: Ingenix, Inc., Eden Prairie, MN (US)

( * ) Notice: Subject to any disclaimer, the term of this patent is extended or adjusted under 35 U.S.C. 154(b) by 0 days.

(21) Appl. No.: 11/841,439

(22) Filed: Aug. 20, 2007

(65) Prior Publication Data

US 2008/0065421 A1 Mar. 13, 2008

Related U.S. Application Data

(60) Continuation of application No. 10/106,626, filed on Mar. 25, 2002, now abandoned, which is a division of application No. 09/188,986, filed on Nov. 9, 1998, now Pat. No. 6,370,511, which is a continuation of application No. 08/493,728, filed on Jun. 22, 1995, now Pat. No. 5,835,897.

(51) Int. Cl.
*A61B 5/00* (2006.01)

(52) U.S. Cl. .................................. 705/3; 705/2; 600/300

(58) Field of Classification Search ...................... 705/2, 705/3; 600/300
See application file for complete search history.

(56) References Cited

U.S. PATENT DOCUMENTS

| | | | |
|---|---|---|---|
| 4,328,491 A | 5/1982 | Demetrescu et al. | |
| 4,667,292 A | 5/1987 | Mohlenbrock et al. | |
| 5,018,067 A * | 5/1991 | Mohlenbrock et al. | 600/300 |
| 5,099,424 A | 3/1992 | Schneiderman | |
| 5,225,976 A | 7/1993 | Tawil | |
| 5,253,164 A | 10/1993 | Holloway et al. | |
| 5,301,105 A | 4/1994 | Cummings, Jr. | |
| 5,307,262 A * | 4/1994 | Ertel | 705/2 |
| 5,324,077 A | 6/1994 | Kessler et al. | |

(Continued)

FOREIGN PATENT DOCUMENTS

WO    WO 95/12857    5/1995

OTHER PUBLICATIONS

Dialoog search history, Mar. 26, 2010.*

(Continued)

*Primary Examiner*—Luke Gilligan
*Assistant Examiner*—Dilek B Cobanoglu
(74) *Attorney, Agent, or Firm*—Dorsey & Whitney LLP

(57) ABSTRACT

A computer-implemented method for profiling medical claims to assist health care managers in determining the cost-efficiency and service quality of health care providers. The method allows an objective means for measuring and quantifying health care services. An episode treatment group (ETG) is a patient classification unit, which defines groups that are clinically homogenous (similar cause of illness and treatment) and statistically stable. The ETG grouper methodology uses service or segment-level claim data as input data and assigns each service to the appropriate episode. The program identifies concurrent and recurrent episodes, flags records, creates new groupings, shifts groupings for changed conditions, selects the most recent claims, resets windows, makes a determination if the provider is an independent lab and continues to collect information until an absence of treatment is detected.

5 Claims, 26 Drawing Sheets

U.S. PATENT DOCUMENTS

| | | | | |
|---|---|---|---|---|
| 5,325,293 | A * | 6/1994 | Dorne | 705/2 |
| 5,365,425 | A | 11/1994 | Torma et al. | |
| 5,483,443 | A * | 1/1996 | Milstein et al. | 705/3 |
| 5,486,999 | A * | 1/1996 | Mebane | 705/2 |
| 5,508,912 | A | 4/1996 | Schneiderman | |
| 5,557,514 | A * | 9/1996 | Seare et al. | 705/2 |
| 5,826,237 | A * | 10/1998 | Macrae et al. | 705/2 |
| 5,845,253 | A * | 12/1998 | Rensimer et al. | 705/2 |
| 5,855,395 | A | 1/1999 | Foote et al. | |
| 5,918,208 | A * | 6/1999 | Javitt | 705/2 |
| 6,182,047 | B1 * | 1/2001 | Dirbas | 705/3 |
| 7,222,079 | B1 * | 5/2007 | Seare et al. | 705/3 |

OTHER PUBLICATIONS

Dialog search results, Mar. 26, 2010.*

Mainour, Arch G., et al. "Antibiotics for Colds in Children who are the High Prescribers?", American Journal of Diseases of Children, Apr. 1998.

Cave, Douglas G., Ph.D. MPH, 1994, "Pattern-of-Treatment Differences Among Primary Care Physicians in Alternative Systems of Care", *Benefits Quarterly*, 10(3):6-19.

* cited by examiner

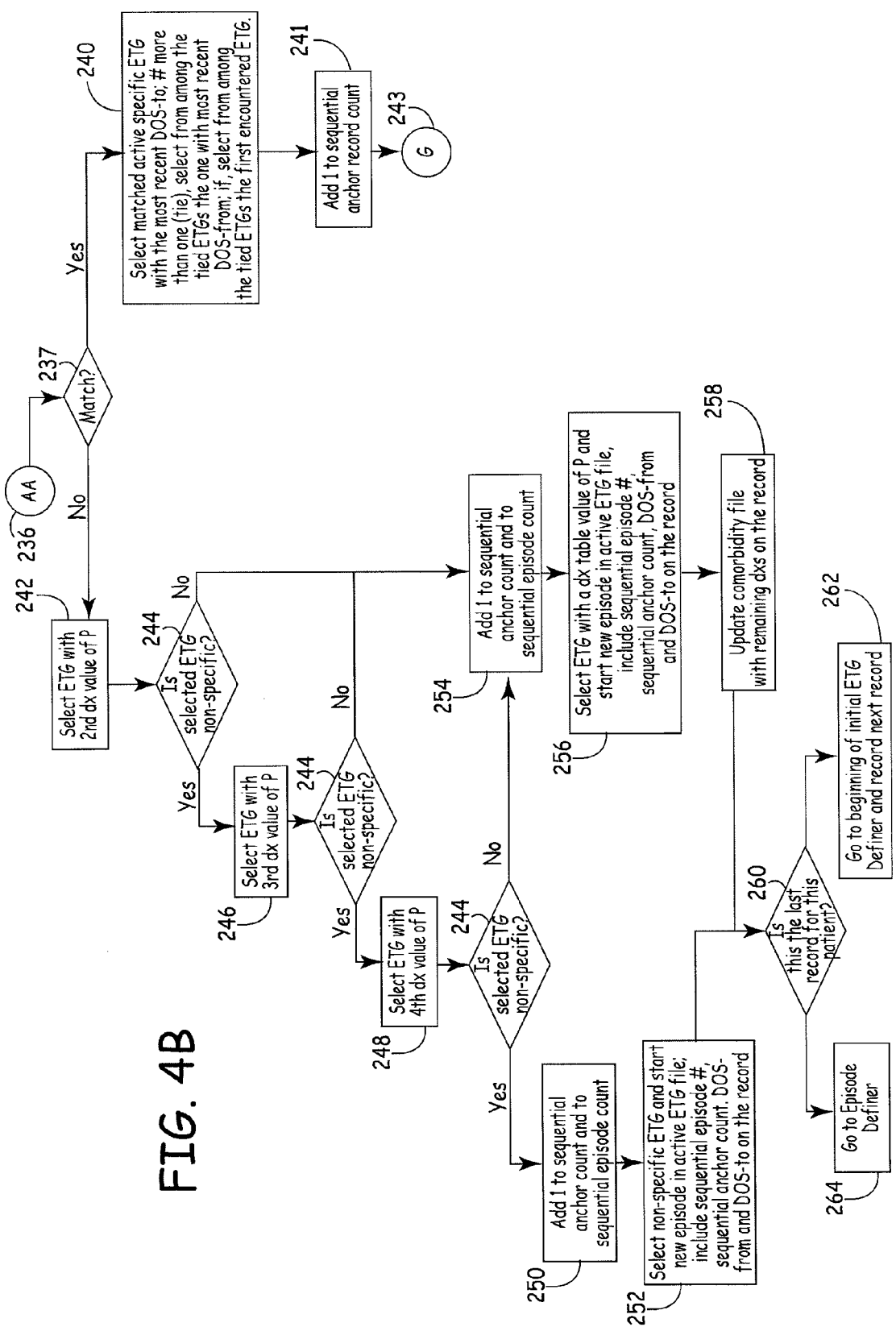

| ETG | ..... | 265 | 266 | ..... | 400 | 401 | 402 | 404 | .... |
|---|---|---|---|---|---|---|---|---|---|
| Dx Code | | | | | | | | | |
| 162 | | | | | C1 | P | A1 | S | |
| 2122 | | | | | I | I | I | P | |
| ... | | | | | | | | | |
| ... | | | | | | | | | |
| ... | | | | | | | | | |
| ... | | | | | | | | | |
| ... | | | | | | | | | |
| 414.8 | | P | S | | | | | | |
| 415 | | I | P | | | | | | |

FIG. 11

| | .... | ETD | ETG | ETG | ETG | .... |
|---|---|---|---|---|---|---|
| Surgery Code | ... | 400 | 401 | 402 | 404 | .... |
| 31766 | | W2 | R2 | W1 | R1 | |

FIG. 12

| NDC | GDC |
|---|---|
| ... | |
| ... | |
| 00002510501 | 40973 |
| 00002510501 | 40973 |
| 61392028990 | 35472 |
| 00002505818 | 39713 |
| 00002505818 | 39713 |
| 61392028990 | 35472 |
| 61392028990 | 35472 |
| 0000203529 | 16192 |
| 0000203528 | 16192 |
| 61392028990 | 35472 |

FIG. 13

| GDC | ETG | RANK |
|---|---|---|
| 40973 | 450 | P1 |
| 39713 | 329 | I1 |
| 39713 | 328 | P1 |
| 39713 | 373 | P7 |
| 39713 | 390 | A7 |
| 39713 | 374 | S7 |
| 16192 | 900 | P1 |
| 40973 | 450 | P2 |
| 35472 | 46 | P6 |
| 35472 | 648 | S7 |

FIG. 14

COMPUTER-IMPLEMENTED METHOD FOR GROUPING MEDICAL CLAIMS BASED UPON CHANGES IN PATIENT CONDITION

CROSS-REFERENCE TO RELATED APPLICATION

This application is a continuation application of U.S. patent application Ser. No. 10/106,626, filed Mar. 25, 2002, which is a divisional application of U.S. patent application Ser. No. 09/188,986, filed Nov. 9, 1998, issued as U.S. Pat. No. 6,370,511, issued on Apr. 9, 2002, which is a continuation patent application of U.S. patent application Ser. No. 08/493,728, filed on Jun. 22, 1995, issued as U.S. Pat. No. 5,835,897 on Nov. 10, 1998, subject matters of which are incorporated by reference herein in their entirety.

FIELD OF THE INVENTION

The present invention relates generally to computer-implemented methods for processing medical claims information. More particularly, the present invention relates to a computer-implemented method for receiving input data relating to a person's medical claim, establishing a management record for the person, establishing episode treatment groups to define groupings of medical episodes of related etiology, correlating subsequent medical claims events to an episode treatment group and manipulating episode treatment groups based upon time windows for each medical condition and co-morbidities.

BACKGROUND OF THE INVENTION

Due to an increase in health care costs and inefficiency in the health care system, health care providers and service management organizations need health care maintenance systems which receive input medical claim data, correlate the medical claim data and provide a means for quantitatively and qualitatively analyzing provider performance. Because of the complex nature of medical care service data, many clinicians and administrators are not able to efficiently utilize the data. A need exists for a computer program that transforms inpatient and out patient claim data to actionable information, which is logically understood by clinicians and administrators.

Performance is quickly becoming the standard by which health care purchasers and informed consumers select their health care providers. Those responsible for the development and maintenance of provider networks search for an objective means to measure and quantify the health care services provided to their clients. Qualitative and quantitative analysis of medical provider performance is a key element for managing and improving a health care network. Operating a successful health care network requires the ability to monitor and quantify medical care costs and care quality. Oftentimes, success depends on the providers' ability to identify and correct problems in their health care system. A need exists, therefore, for an analytical tool for identifying real costs in a given health care management system.

To operate a more efficient health care system, health care providers need to optimize health care services and expenditures. Many providers practice outside established utilization and cost norms. Systems that detect inappropriate coding, eliminate potentially inappropriate services or conduct encounter-based payment methodology are insufficient for correcting the inconsistencies of the health care system. When a complication or comorbidity is encountered during the course of treatment, many systems do not reclassify the treatment profile. Existing systems do not adjust for casemix, concurrent conditions or recurrent conditions. A system that compensates for casemix should identify the types of illnesses treated in a given population, determine the extent of resource application to specific types of illnesses, measure and compare the treatment patterns among individual and groups of health care providers and educate providers to more effectively manage risk. When profiling claims, existing systems establish classifications that do not contain a manageable number of groupings, are not clinically homogeneous or are not statistically stable. A need exists, therefore, for a patient classification system that accounts for differences in patient severity and establishes a clearly defined unit of analysis.

For many years, computer-implemented programs for increasing health care efficiency have been available for purchase. Included within the current patent literature and competitive information are many programs that are directed to the basic concept of health care systems.

The Mohlenbrock, et al., U.S. Pat. No. 4,667,292, issued in 1987, discloses a medical reimbursement computer system which generates a list identifying the most appropriate diagnostic-related group (DRG) and related categories applicable to a given patient for inpatient claims only. The list is limited by a combination of the characteristics of the patient and an initial principal diagnosis. A physician can choose a new designation from a list of related categories while the patient is still being treated. The manually determined ICD-9 numbers can be applied to an available grouper computer program to compare the working DRG to the government's DRG.

The Mohlenbrock, et al., U.S. Pat. No. 5,018,067, issued in 1991, discloses an apparatus and method for improved estimation of health resource consumption through the use of diagnostic and/or procedure grouping and severity of illness indicators. This system is a computer-implemented program that calculates the amount of payment to the health provider by extracting the same input data as that identified in the Mohlenbrock '292 patent teaching the DRG System. The system calculates the severity of the patient's illness then classifies each patient into sub-categories of resource consumption within a designated DRG. A computer combines the input data according to a formula consisting of constants and variables. The variables are known for each patient and relate to the number of ICD codes and the government weighing of the codes. The software program determines a set of constants for use in the formula for a given DRG that minimizes variances between the actual known outcomes and those estimated by use of the formula. Because it is based upon various levels of illness severity within each diagnosis, the results of this system provide a much more homogenous grouping of patients than is provided by the DRGs. Providers can be compared to identify those providers whose practice patterns are of the highest quality and most cost efficient. A set of actual costs incurred can be compared with the estimated costs. After the initial diagnosis, the system determines the expected costs of treating a patient.

The Schneiderman U.S. Pat. No. 5,099,424, issued in 1992, discloses a model user application system for clinical data processing that tracks and monitors a simulated outpatient medical practice using database management software. The system allows for a database of patients and the entry of EKG and/or chest x-ray (CXR) test results into separate EKG/CXR records as distinct logical entities. This system requires entry of test results that are not part of the medical claim itself. If not already present, the entry creates a separate lab record that may be holding blood work from the same lab test request. Portions of the information are transferred to the lab record for all request situations. Although the lab record data routine is limited to blood work, each time the routine is run, historical parameter data are sent to a companion lab record along with other data linking both record types. The system also includes a revision of the system's specialist record and the general recommendation from an earlier work for more explicit use in information management.

The Tawil U.S. Pat. No. 5,225,976, issued in 1993, discloses an automated health benefit processing system. This system minimizes health care costs by informing the purchasers of medical services about market conditions of those medical services. A database includes, for each covered medical procedure in a specific geographic area, a list of capable providers and their charges. A first processor identifies the insured then generates a treatment plan and the required medical procedures. Next, the first processor retrieves information related to the medical procedures and appends the information to the treatment plan. A second processor generates an actual treatment record including the actual charges. A third processor compares the plan and the actual records to determine the amounts payable to the insured and the provider.

The Ertel U.S. Pat. No. 5,307,262, issued in 1994, discloses a patient data quality review method and system. The system performs data quality checks and generates documents to ensure the best description of a case. The system provides file security and tracks the cases through the entire review process. Patient data and system performance data are aggregated into a common database that interfaces with existing data systems. Data profiles categorize data quality problems by type and source. Problems are classified as to potential consequences. The system stores data, processes it to determine misreporting, classifies the case and displays the case-specific patient data and aggregate patient data.

The Holloway, et al., U.S. Pat. No. 5,253,164, issued in 1993, discloses a system and method for detecting fraudulent medical claims via examination of service codes. This system interprets medical claims and associated representation according to specific rules and against a predetermined CPT-4 code database. A knowledge base interpreter applies the knowledge base using the rules specified. The database can be updated as new methods of inappropriate coding are discovered. The system recommends appropriate CPT codes or recommends pending the claims until additional information is received. The recommendations are based on the decision rules that physician reviewers have already used on a manual basis.

The Cummings U.S. Pat. No. 5,301,105, issued in 1994, discloses an all care health management system. The patient-based system includes an integrated interconnection and interaction of essential health care participants to provide patients with complete support. The system includes interactive participation with the patients employers and banks. The system also integrates all aspects of the optimization of health-inducing diet and life style factors and makes customized recommendations for health-enhancing practices. By pre-certifying patients and procedures, the system enhances health care efficiency and reduces overhead costs.

The Dorne U.S. Pat. No. 5,325,293, issued in 1994, discloses a system and method for correlating medical procedures and medical billing codes. After an examination, the system automatically determines raw codes directly associated with all of the medical procedures performed or planned to be performed with a particular patient. The system allows the physician to modify the procedures after performing the examination. By manipulating the raw codes, the system generates intermediate and billing codes without altering the raw codes.

The Kessler, et al., U.S. Pat. No. 5,324,077, issued in 1994, discloses a negotiable medical data draft for tracking and evaluating medical treatment. This system gathers medical data from ambulatory visits using a medical data draft completed by the provider to obtain payment for services, to permit quality review by medical insurers. In exchange for immediate partial payment of services, providers are required to enter data summarizing the patient's visit on negotiable medical drafts. The partial payments are incentives to providers for participating in the system.

The Torma, et al., U.S. Pat. No. 5,365,425, issued in 1994, discloses a method and system for measuring management effectiveness. Quality, cost and access are integrated to provide a holistic description of the effectiveness of care. The system compares general medical treatment databases and surveyed patient perceptions of care. Adjustments based on severity of illness, case weight and military costs are made to the data to ensure that all medical facilities are considered fairly.

Health Chex's PEER-A-MED computer program is a physician practice profiling system that provides case-mix adjusted physician analysis based on a clinical severity concept. The system employs a multivariate linear regression analysis to appropriately adjust for case-mix. After adjusting for the complexity of the physician's caseload, the system compares the relative performance of a physician to the performance of the peer group as a whole. The system also compares physician utilization performance for uncomplicated, commonly seen diagnosis. Because the full spectrum of clinical care that is rendered to a patient is not represented in its databases, the system is primarily used as an economic performance measurement tool. This system categorizes the claims into general codes including acute, chronic, mental health and pregnancy. Comorbidity and CPT-4 codes adjust for acuity level. The codes are subcategorized into twenty cluster groups based upon the level of severity. The system buckets the codes for the year and contains no apparent episode building methodology. While the PEER-A-MED system contains clinically heterogeneous groupings, the groupings are not episode-based and recurrent episodes cannot be accounted.

Ambulatory Care Groups (ACG) provides a patient-based system that uses the patient and the analysis unit. Patients are assigned to an diagnosis group and an entire year's claims are bucketed into thirty-one diagnosis groups. By pre-defining the diagnosis groups, this is a bucketing-type system and claim management by medical episode does not occur. The system determines if a claim is in one of the buckets. Because different diseases could be categorized into the same ACG, this system is not clinically homogeneous. An additional problem with ACGs is that too many diagnosis groups are in each ACG.

Ambulatory Patient Groups (APGs) are a patient classification system designed to explain the amount and type of resources used in an ambulatory visit. Patients in each APG have similar clinical characteristics and similar resource use and cost. Patient characteristics should relate to a common organ system or etiology. The resources used are constant and predictable across the patients within each APG. This system is an encounter-based system because it looks at only one of the patient's encounters with the health care system. This system mainly analyzes outpatient hospital visits and does not address inpatient services.

The GMIS system uses a bucketing procedure that profiles by clumps of diagnosis codes including 460 diagnostic episode clusters (DECs). The database is client specific and contains a flexible number and type of analytic data files. This system is episode-based, but it does not account for recurrent episodes, so a patient's complete data history within a one-year period is analyzed as one pseudo-episode. Signs and symptoms do not cluster to the actual disease state, e.g. abdominal pain and appendicitis are grouped in different clusters. This system does not use CPT-4 codes and does not shift the DEC to account for acuity changes during the treatment of a patient.

Value Health Sciences offers a value profiling system, under the trademark VALUE PROFILER, which utilizes a DB2 mainframe relational database with 1,800 groups. The system uses ICD9 and CPT-4 codes, which are bucket codes. Based on quality and cost-effectiveness of care, the system evaluates all claims data to produce case-mix-adjusted profiles of networks, specialties, providers and episodes of illness. The pseudo-episode building methodology contains clinically pre-defined time periods during which claims for a patient are associated with a particular condition and designated provider. The automated practice review system analyzes health care claims to identify and correct aberrant claims in a pre-payment mode (Value Coder) and to profile practice patterns in a post-payment mode (Value Profiler). This system does not link signs and symptoms and the diagnoses are non-comprehensive because the profiling is based on the exclusion of services. No apparent shifting of episodes occurs and the episodes can only exist for a preset time because the windows are not recurrent.

The medical claim profiling programs described in foregoing patents and non-patent literature demonstrate that, while conventional computer-implemented health care systems exist, they each suffer from the principal disadvantage of not identifying and grouping medical claims on an episodic basis or shifting episodic groupings based upon complications or co-morbidities. The present computer-implemented health care system contains important improvements and advances upon conventional health care systems by identifying concurrent and recurrent episodes, flagging records, creating new groupings, shifting groupings for changed clinical conditions, selecting the most recent claims, resetting windows, making a determination if the provider is an independent lab and continuing to collect information until an absence of treatment is detected.

SUMMARY OF THE INVENTION

Accordingly, it is a broad aspect of the present invention to provide a computer-implemented medical claims profiling system.

It is a further object of the present invention to provide a medical claims profiling system that allows an objective means for measuring and quantifying health care services.

It is a further object of the present invention to provide a medical claims profiling system that includes a patient classification system based upon episode treatment groups.

It is a further object of the present invention to provide a medical claims profiling system that groups claims to clinically homogeneous and statistically stable episode treatment groups.

It is a further object of the present invention to provide a medical claims profiling system that includes claims grouping utilizing service or segment-level claim data as input data.

It is a further object of the present invention to provide a medical claims profiling system that assigns each claim to an appropriate episode.

It is a further object of the present invention to provide a medical claims profiling system that identifies concurrent and recurrent episodes.

It is a further object of the present invention to provide a medical claims profiling system that shifts groupings for changed clinical conditions.

It is a further object of the present invention to provide a medical claims profiling system that employs a decisional tree to assign claims to the most relevant episode treatment group.

It is a further object of the present invention to provide a medical claims profiling system that resets windows of time based upon complications, co-morbidities or increased severity of clinical conditions.

It is a further object of the present invention to provide a health care system that continues to collect claim information and assign claim information to an episode treatment group until an absence of treatment is detected.

It is a further object of the present invention to provide a health care system that creates orphan records.

It is a further object of the present invention to provide a health care system that creates phantom records.

The foregoing objectives are met by the present system that allows an objective means for measuring and quantifying health care services based upon episode treatment groups (ETGs). An episode treatment group (ETG) is a clinically homogenous and statistically stable group of similar illness etiology and therapeutic treatment. ETG grouper method uses service or segment-level claim data as input data and assigns each service to the appropriate episode.

ETGs gather all in-patient, ambulatory and ancillary claims into mutually exclusive treatment episodes, regardless of treatment duration, then use clinical algorithms to identify both concurrent and recurrent episodes. ETG grouper method continues to collect information until an absence of treatment is detected for a predetermined period of time commensurate with the episode. For example, a bronchitis episode will have a sixty-day window, while a myocardial infarction may have a one-year window. Subsequent records of the same nature within the window reset the window for an additional period of time until the patient is asymptomatic for the pre-determined time period.

ETGs can identify a change in the patients condition and shift the patient's episode from the initially defined ETG to the ETG that includes the change in condition. ETGs identify all providers treating a single illness episode, allowing the user to uncover specific treatment patterns. After adjusting for case-mix, ETGs measure and compare the financial and clinical performance of individual providers or entire networks.

Medical claim data is input as data records by data entry into a computer storage device, such as a hard disk drive. The inventive medical claims profiling system may reside in any of a number of computer system architectures, i.e., it may be run from a stand-alone computer or exist in a client-server system, for example a local area network (LAN) or wide area network (WAN).

Once relevant medical claim data is input, claims data is processed by loading the computer program into the computer system memory. During set-up of the program onto the computer system, the computer program will have previously set pointers to the physical location of the data files and look-up tables written to the computer storage device. Upon initialization of the inventive computer program, the user is prompted to enter an identifier for a first patient. The program then checks for open episodes for the identified patient, sets flags to identify the open episodes and closes any episodes based upon a predetermined time duration from date of episode to current date. After all open episodes for a patient are identified, the new claims data records are read to memory and validated for type of provider, CPT code and ICD-9 (dx) code, then identified as a management, surgery, facility, ancillary, drug or other record.

As used herein, "Management records" are defined as claims that represent a service by a provider engaging in the direct evaluation, management or treatment or a patient. Examples of management records include office visits and therapeutic services. Management records serve as anchor records because they represent focal points in the patient treatment as well as for related ancillary services.

"Ancillary records" are claims which represent services which are incidental to the direct evaluation, management and treatment of the patient. Examples of ancillary records include X-ray and laboratory tests.

"Surgery records" are specific surgical claims. Surgery records also serve as anchor records.

"Facility records" are claims for medical care facility usage. Examples of facility records include hospital room charges or outpatient surgical room charges.

"Drug records" are specific for pharmaceutical prescription claims.

"Other records" are those medical claim records which are not management, surgery, ancillary, facility or drug records.

Invalid records are flagged and logged to an error output file for the user. Valid records are then processed by an ETG Assignor Sub-routine and, based upon diagnosis code, is either matched to existing open episodes for the patient or serve to create new episodes.

Management and surgery records serve as "anchor records." An "anchor record" is a record which originates a diagnosis or a definitive treatment for a given medical condition. Management and surgery records serve as base reference records for facility, ancillary and drug claim records relating to the diagnosis or treatment which is the subject of the management or surgery record. Only management and surgery records can serve to start a given episode.

If the record is a management record or a surgery record, the diagnosis code in the claim record is compared with prior related open episodes in an existing look-up table for a possible ETG match. If more than one open episode exists, the program selects the most recent open episode. A positive match signifies that the current episode is related to an existing open episode. After the match is determined, the time window is reset for an additional period of time corresponding to the episode. A loop shifts the originally assigned ETG based on the additional or subsequent diagnoses. If any of the additional or subsequent diagnoses is a defined co-morbidity diagnosis, the patient's co-morbidity file updated. If no match between the first diagnosis code and an open episode is found, a new episode is created.

Grouping prescription drug records requires two tables, a NDC (National Drug Code) by GDC (Generic Drug Code) table and a GDC by ETG table. Because the NDC table has approximately 200,000 entries, it has been found impracticable to directly construct an NDC by ETG table. For this reason the NDC by GDC table serves as a translation table to translate NDCs to GDCs and construct a smaller table based upon GDCs. Reading, then from these tables, the NDC code in the claim data record is read and translated to a GDC code. The program then identifies all valid ETGs for the GDC codes in the claim data record then matches those valid ETGs with active episodes.

These and other objects, features and advantages of the present invention will become more apparent to those skilled in the art from the following more detailed description of the non-limiting preferred embodiment of the invention taken with reference to the accompanying Figures.

BRIEF DESCRIPTION OF THE DRAWINGS

Briefly summarized, a preferred embodiment of the invention is described in conjunction with the illustrative disclosure thereof in the accompanying drawings, in which:

FIGS. 4A to 4F are flow diagrams illustrating the Management Record Grouping Sub-routine of the ETG Assignor Routine in accordance with the computer-implemented method of the present invention.

FIG. 11 is a diagrammatic representation of a I-9 Diagnosis Code (dx) X ETG table illustrating predetermined table values called by the Episode Definer Routine of the present invention.

FIG. 12 is a diagrammatic representation of an I-9 Diagnosis Code 9 (dx) X CPT Code table illustrating predetermined table values called by the Episode Definer Routine of the present invention.

FIG. 13 is a diagrammatic representation of a National Drug Code (NDC) to Generic Drug Code (GDC) conversion table illustrating predetermined Generic Drug Code values called by the Drug Record Grouping Sub-routine of the Episode Definer Routine of the present invention.

FIG. 14 is a diagrammatic representation of a Generic Drug Code (GDC) to Episode Treatment Group (ETG) table illustrating predetermined table values called by the Drug Record Grouping Sub-routine of the Episode Definer Routine of the present invention.

DETAILED DESCRIPTION OF THE PREFERRED EMBODIMENT

Figure 1:
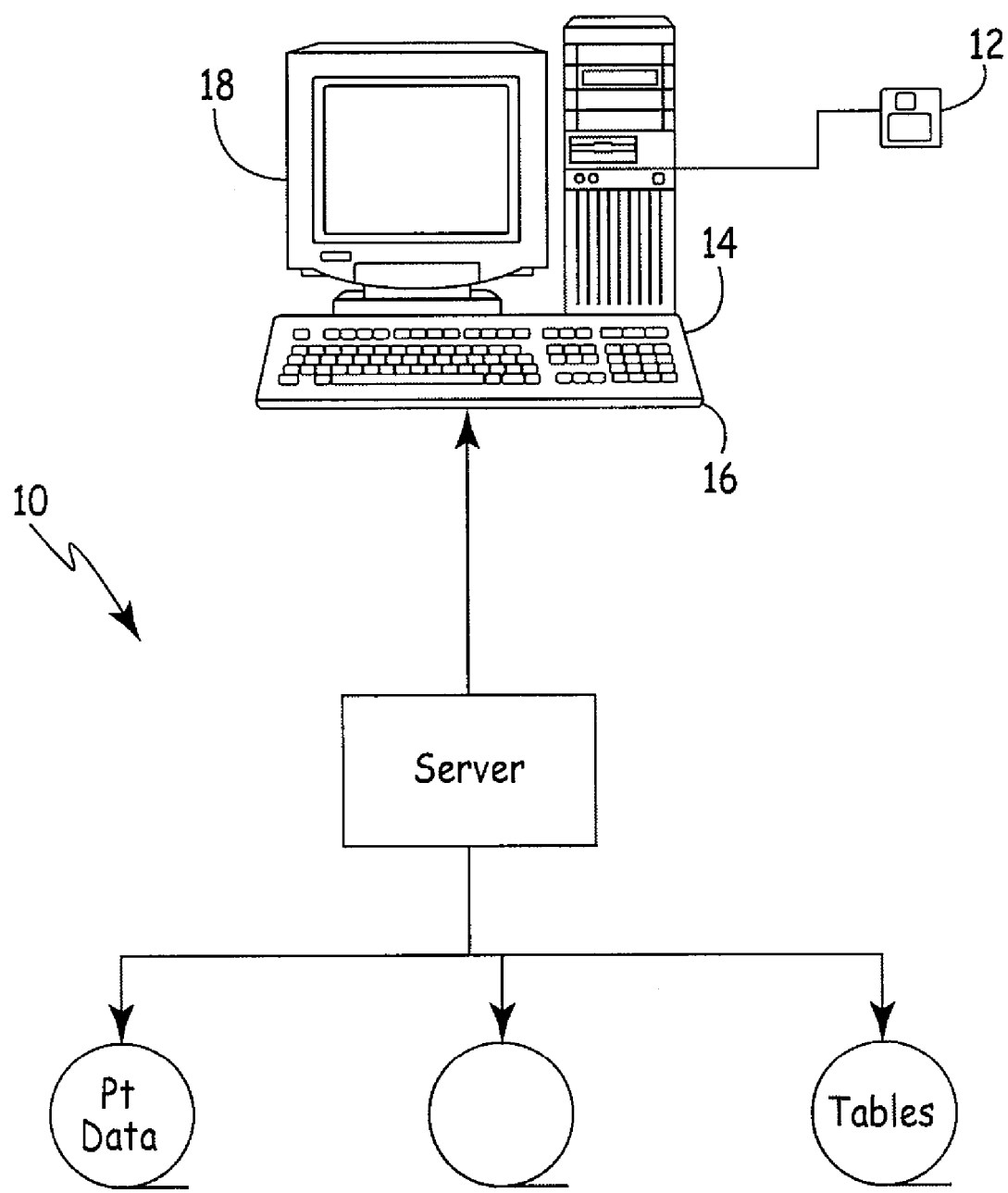
FIG. 1 is a diagrammatic representation of a computer system used with the computer-implemented method for analyzing medical claims data in accordance with the present invention.

Referring particularly to the accompanying drawings, the basic structural elements of a health care management system of the present invention are shown. Health care management system consists generally of a computer system 10. Computer system 10 is capable of running a computer program 12 that incorporates the inventive method is shown in FIG. 1. The computer system 10 includes a central processing unit (CPU) 14 connected to a keyboard 16 which allows the user to input commands and data into the CPU 14. It will be understood by those skilled in the art that CPU 14 includes a microprocessor, random access memory (RAM), video display controller boards and at least one storage means, such as a hard disk drive or CD-ROM. The computer system 10 also contains a video display 18 which displays video images to a person using the computer system 10. The video display screen 18 is capable of displaying video output in the form of text or other video images.

Episode Treatment Groups (ETGs) are used to define the basic analytical unit in the computer-implemented method of the present invention. ETGs are episode based and conceptually similar to Diagnostic Related Groups (DRGs), with a principal difference being that DRGs are inpatient only. ETGs encompass both inpatient and outpatient treatment.

Using ETGs as the basic episodic definer permits the present invention to track concurrently and recurrently occurring illnesses and correctly identify and assign each service event to the appropriate episode. Additionally, ETGs account for changes in a patient's condition during a course of treatment by shifting from the initially defined ETG to one which includes the changed condition once the changed condition is identified.

The inventive medical claims profiling system defines Episode Treatment Groups (ETGs). The number of ETGs may vary, depending upon the definitional specificity the health care management organization desires. Presently, the inventive system defines 558 ETGs, which are assigned ETG Numbers 1-900 distributed across the following medical areas: Infectious Diseases, Endocrinology, Hematology, Psychiatry, Chemical Dependency, Neurology, Opthalmology, Cardiology, Otolaryngology, Pulmonology, Gastroenterology, Hepatology, Nephrology, Obstetrics, Gynecology, Dermatology, Orthopedics and Rheumatology, Neonatology, Preventative and Administrative and Signs and Isolated Signs, Symptoms and Non-Specific Diagnoses or Conditions. Under the presently existing system, ETG 900 is reserved to "Isolated Signs, Symptoms and Non-Specific Diagnoses or Conditions," and is an ETG designation used where the diagnosis code is incapable of being assigned to another ETG. A listing of exemplary ETGs for typical episodes is found at Table 1, below. Those skilled in the art will understand, however, that the number of ETGs may change, the ETG numbering system is variable, the ETG classifications may be defined with relatively broader or narrower degrees of specificity and the range of medical specialties may be greater or fewer, as required may be require by the management organization in their medical claims data analysis protocols.

An episode may be considered a low outlier or high outlier. Low outliers are episodes with dollar values below the minimum amount which is specific to each ETG. Examples of low outliers include patients which drop from a plan during mid-episode and patients who use out-of-network providers and do not submit claims. High outliers are those episodes with high dollar values greater than the 75th percentile plus 2.5 times the interquartile range, based upon a predefined database. The low and high outlier points are pre-determined and hard-coded into the inventive system and will vary across analysis periods.

If no ICD-9 (diagnosis code) on a given record matches the CPT-4 code, i.e., a diagnosis of bronchitis and a CPT of knee x-ray, an invalid code segment results. The inventive system outputs invalid records and discontinues the processing of these records. An invalid ICD-9 code is assigned to ETG 997, an invalid CPT-4 code is assigned to ETG 996 and an invalid provider type is assigned to ETG 995. A sequential anchor count and a sequential episode count are incremented after each ETG assignment. Active open and closed ETG files include ETG number, sequential episode number, most recent anchor from date of service and most recent sequential anchor record count. An alternative embodiment creates a single record for each individual episode containing ETG number, patient age, patient sex, episode number, total charges, total payments, earlier anchor record, last anchor record, whether the episode was closed ("clean finish"), number of days between database start date and earliest anchor record, whether a number of days between database start date and earliest anchor record exceeds the ETG's days interval, patient identification, physician identification, management charges, management paid, surgery charges, surgery paid, ancillary charges and ancillary paid.

The inventive system uses clinical algorithms to identify both concurrent and recurrent episodes. Subsequent episodes of the same nature within a window reset the window for an additional period of time until the patient is asymptomatic for a pre-determined time period. If an ETG matches a prior ETG, a recurrent ETG is created and the window is reset. The most recent claim is selected if more than one matched claim exists. If the ETG does not match an active ETG, a new concurrent ETG is created.

Comorbidities, complications or a defining surgery could require an update of the patient's condition to an ETG requiring a more aggressive treatment profile. ETG's changes in the patient's clinical condition and shift the patient's episode from the initially defined ETG to an ETG which includes the change in clinical condition.

If the claim is an ancillary record and it does not match an active ETG it is designated an "orphan" ancillary record.

Termination of an episode is detected by an absence of treatment for a period of time commensurate with the episode.

If the claim is a prescription drug record, two pre-defined tables written to the computer data storage medium, are read. The first of the tables is a National Drug Code (NDC) by Generic Drug Code (GDC) table. The GDC code is equivalent to the Generic Drug Code table known in the art. This table acts as a translator table to translate a large number of NDCs to a smaller set of GCNs. A second pre-defined table is employed and is constructed as a GDC by ETG table. The GDC by ETG table is used, in conjunction with the NDC by GDC translator table, to identify all valid ETGs for a particular NDC code in the claim record.

To determine specific treatment patterns and performance contributions, the computer-implemented method identifies all providers treating a single illness episode. If a network of providers contains Primary Care Physicians (PCP), the ETGs clearly identify each treatment episode by PCP. Financial and clinical performance of individual providers or entire networks may be monitored and analyzed. To monitor health care cost management abilities of providers, components of a provider's treatment plan may be analyzed by uncovering casemix-adjusted differences in direct patient management, the use of surgery and the prescribing of ancillary services. By identifying excessive utilization and cost areas, continuous quality improvement protocols are readily engineered based on internally or externally derived benchmarks. After adjusting for location and using geographically derived normative charge information, ETG-based analysis compares the cost performance of providers or entire networks. By using geographically derived utilization norms, the present invention forms the methodology base for measuring both prevalence and incidence rates among a given population by quantifying health care demand in one population and comparing it to external utilization norms. This comparison helps to identify health care providers who practice outside established utilization or cost norms.

Figure 2:
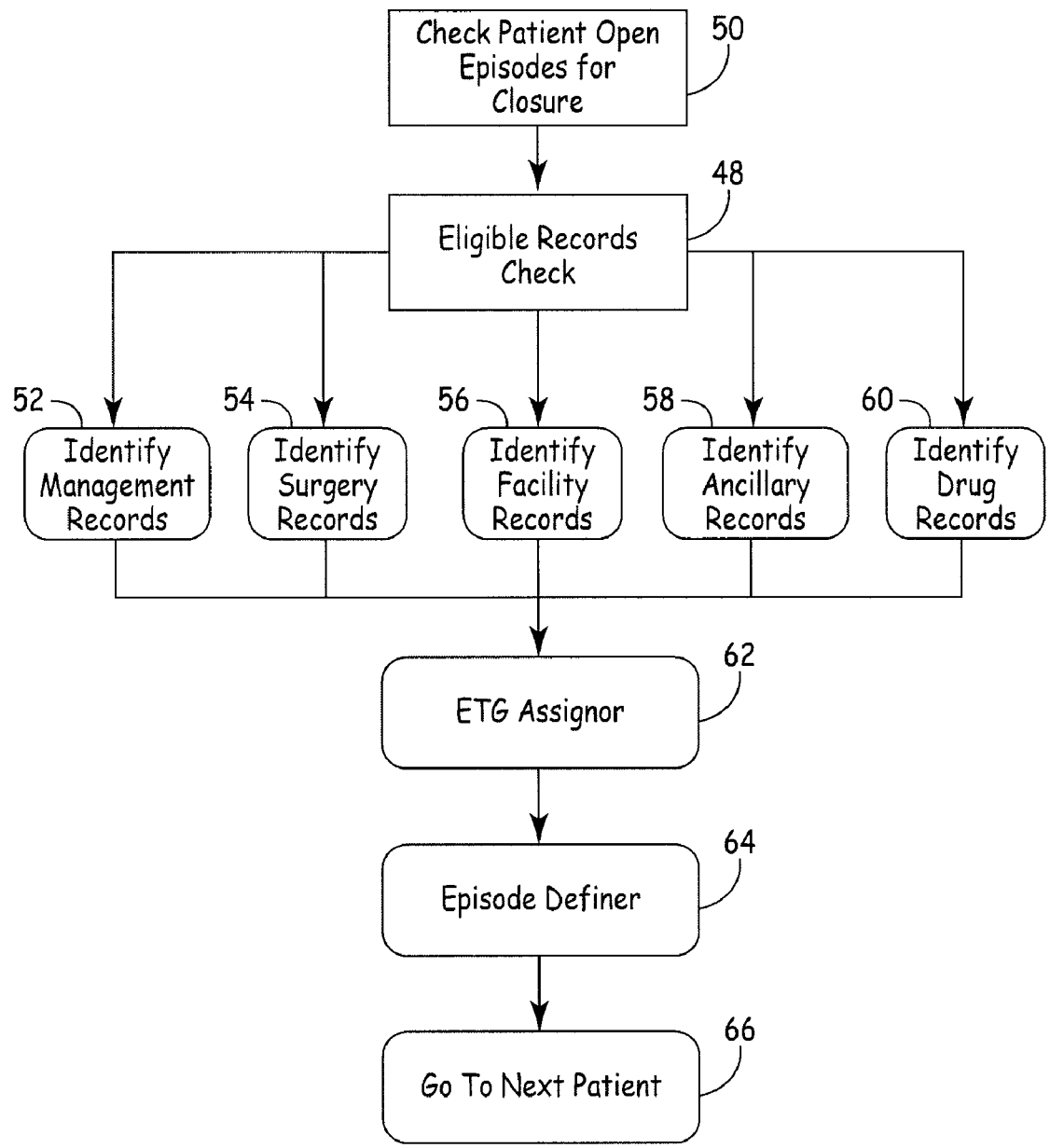
FIG. 2 is a flow diagram illustrating the general functional steps of the computer implemented method for analyzing medical claims data in accordance with the present invention.

Turning now to FIG. 2, there is illustrated the general operation of the computer-implemented method of the present invention. Those skilled in the art will understand that the present invention is first read from a removable, transportable recordable medium, such as a floppy disk, magnetic tape or a CD-ROM onto a recordable, read-write medium, such as a hard disk drive, resident in the CPU 14. Upon a user's entry of appropriate initialization commands entered via the keyboard 16, or other input device, such as a mouse or trackball device, computer object code is read from the hard disk drive into the memory of the CPU 14 and the computer-implemented method is initiated. The computer-implemented method prompts the user by displaying appropriate prompts on display 18, for data input by the user.

Those familiar with medical claims information processing will understand that medical claims information is typically received by a management service organization on paper forms. If this is the case, a user first manually sorts claim records by patient, then input patient data through interfacing with the CPU 14 through the keyboard 16 or other input device.

Prior to being submitted to the grouping algorithm, records must be sorted by patient by chronological date of service. An Eligible Record Check routine 48 to verify the validity and completeness of the input data. As each record is read by the software, it first checks the date of service on the record and compares it to the last service date of all active episodes to evaluate which episodes have expired in terms of an absence of treatment. These episodes are closed at step 50. Next the record is identified as either a management 52, surgery 54, facility 56, ancillary 58 or drug 60 record. These types of records are categorized as follows:

"Management records" are defined as claims which represent a service by a provider engaging in the direct evaluation, management or treatment or a patient. Examples of management records include office visits, surgeries and therapeutic services. Management records serve as anchor records because they represent focal points in the patient treatment as well as for related ancillary services.

"Ancillary records" are claims which represent services which are incidental to the direct evaluation, management and treatment of the patient. Examples of ancillary records include X-ray and laboratory tests.

"Surgery records" represent surgical procedures performed by physicians and other like medical allied personnel. Like management records, surgery records also serve as anchor records.

"Facility records" are claims for medical care facility usage. Examples of facility records include hospital room charges or ambulatory surgery room charges.

"Drug records" are specific for pharmaceutical prescription claims.

A "cluster" is a grouping of one, and only one, anchor record, management or surgery, and possibly ancillary, facility and/or drug records. A cluster represents a group of services in which the focal point, and therefore the responsible medical personnel, is the anchor record. An episode is made up of one or more clusters.

After the management, surgery, facility, ancillary and drug records are identified at steps 52, 54, 56, 58 and 60, respectively, an ETG Assignor Sub-routine is executed at step 62. The ETG Assignor Sub-routine 62 assigns patient medical claims to ETGs based one or more cluster of services related to the same episode, and provides for ETG shifting upon encountering a diagnosis code or CPT code which alters the relationship between the diagnosis or treatment coded in the claim record and an existing ETG assignment. For example, ETG's may be shifted to account for changes in clinical severity, for a more aggressive ETG treatment profile if a complication or comorbidity is encountered during the course of treatment for a given ETG or where a defining surgery is encountered during the course of treatment for a given ETG.

When the last claim data record for a given patient is processed by the ETG Assignor Routine 62, the Episode Definer Routine is executed at step 64. Episode Definer Routine 64 identifies all open and closed ETG episodes for the patient and appropriately shifts any episodes to a different ETG if such ETG is defined by age and/or the presence or absence of a co-morbidity. The patient records are then output to a file with each record containing the ETG number, a sequential episode number, and a sequential cluster number. Upon input of an identifier for the next patient, the processing of medical claims for the next patient is initiated at step 66 by looping back to check for eligible records for the new patient at step 48.

Figure 3:
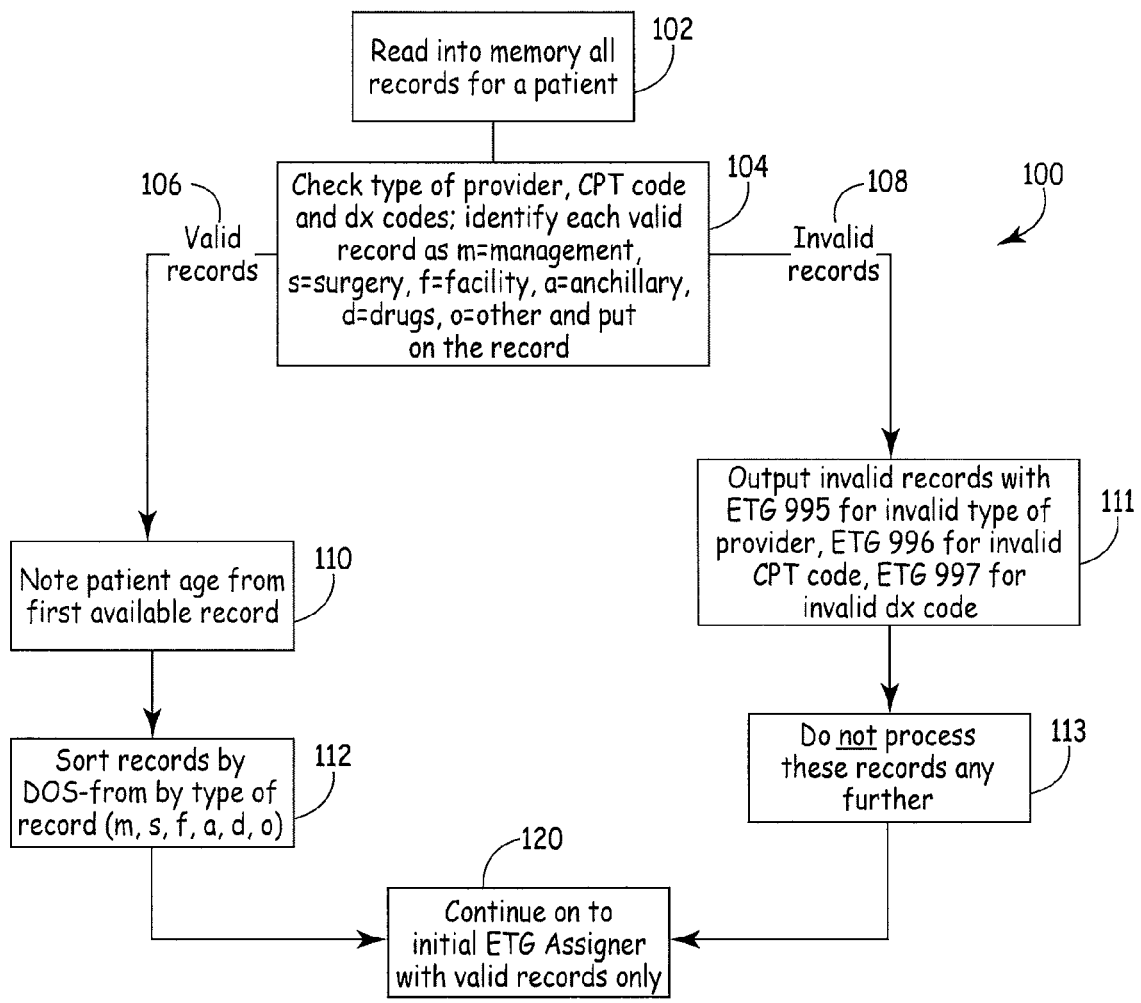
FIG. 3 is a flow diagram illustrating an Eligible Record Check routine which validates and sorts patient claim data records.

Operation of the Eligible Record Check routine 100 is illustrated in FIG. 3. The patient records input by the user are read from the recordable read-write data storage medium into the CPU 14 memory in step 102. From the patient records read to memory in step 102, a record validation step 104 is carried out to check provider type, treatment code and diagnosis code against pre-determined CPT code and diagnosis code look up tables. The diagnosis code is preferably the industry standard ICD-9 code and the treatment code is preferably the industry standard CPT-4 code. All valid patient records are assigned as one of a) management record, b) ancillary record, c) surgery record, d) facility record, e) drug record or f) other record, and coded as follows:

m=management record;
a=ancillary record;
s=surgery record;
f—facility record;
d=drug record; or
o=other record.

A sort of valid records 106 and invalid records 108 from step 104 is made. For valid records 106 in step 110, patient age is then read to memory from the first patient record from step 106. All valid records are then sorted by record type in step 112, i.e., record type m, a, s, f, d or o by a date of service from date (DOS-from). A sort index of all record-type sorted records from step 116 is generated and written to the hard disk, and the ETG Assignor routine 120 is initialized.

For invalid records 108 identified at step 104, the records are assigned ETG designations reserved for records having invalid provider data, invalid treatment code, or invalid diagnosis code, e.g., ETG 995, 996 and 997, respectively, at step 111. An error log file is output identifying the invalid records by reserved ETG and written to disk or displayed for the user and processing of the invalid records terminates at step 113.

Figure 6A:
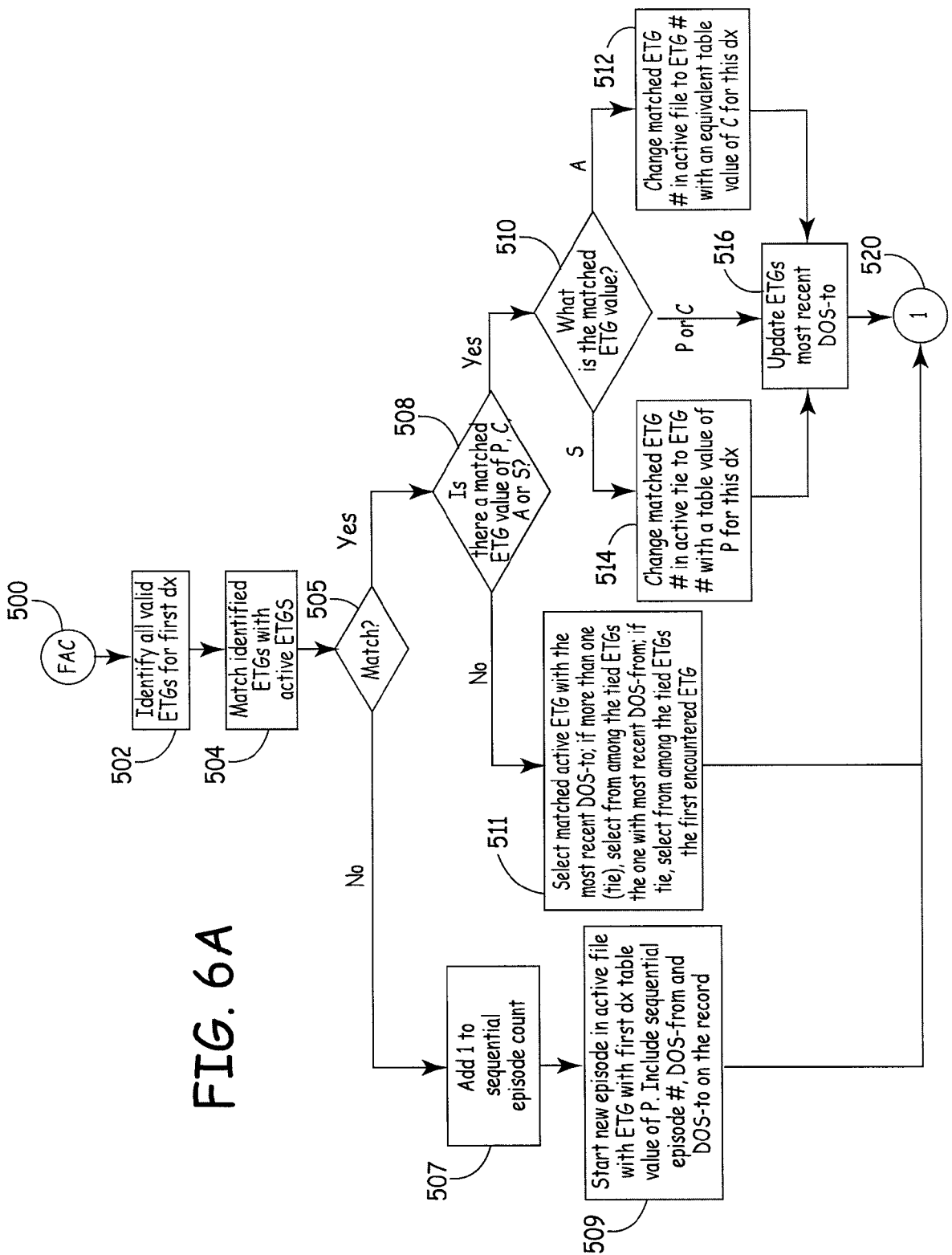
FIGS. 6A-6E are flow diagrams illustrating a Facility Record Grouping Sub-routine of the ETG Assignor Routine in accordance with the computer-implemented method of the present invention.
Figure 6B:
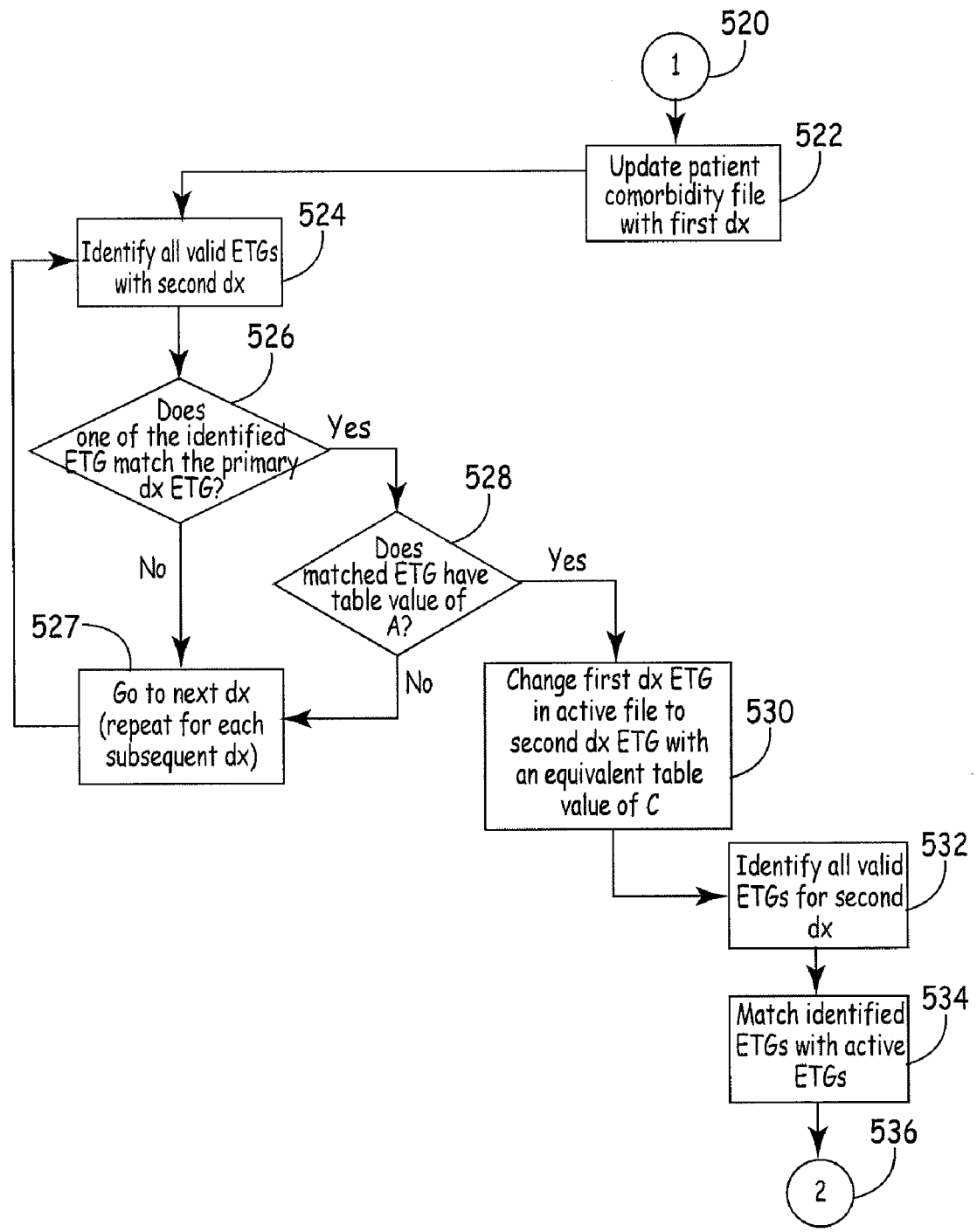
Figure 6C:
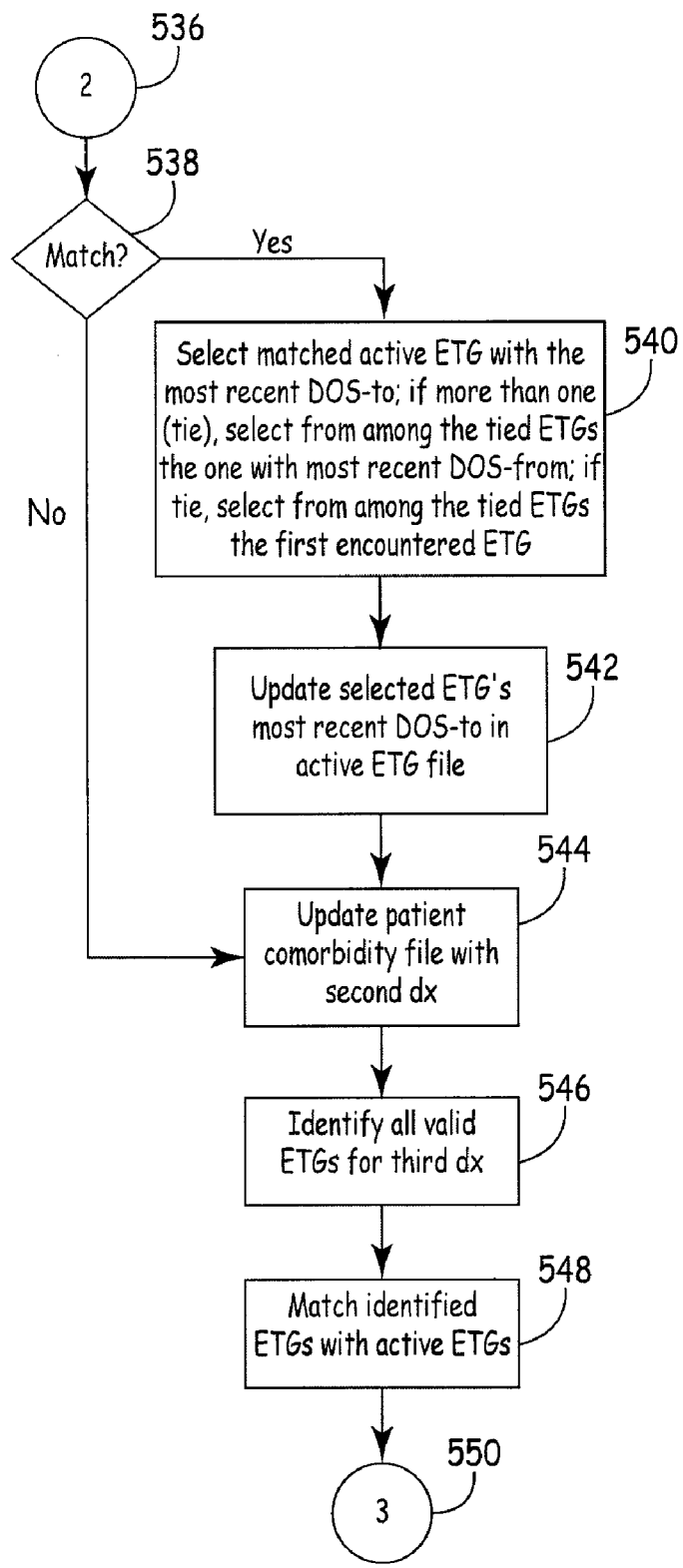
Figure 6D:
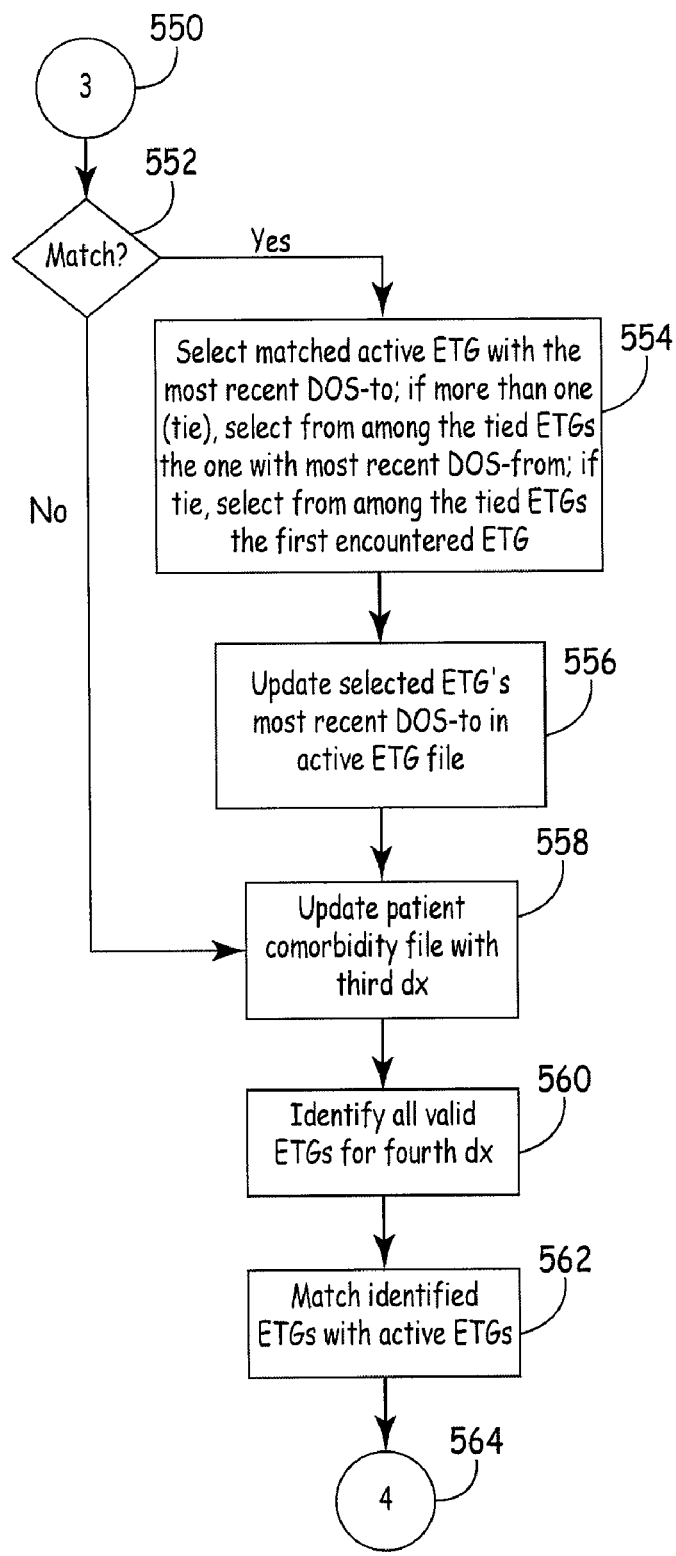
Figure 6E:
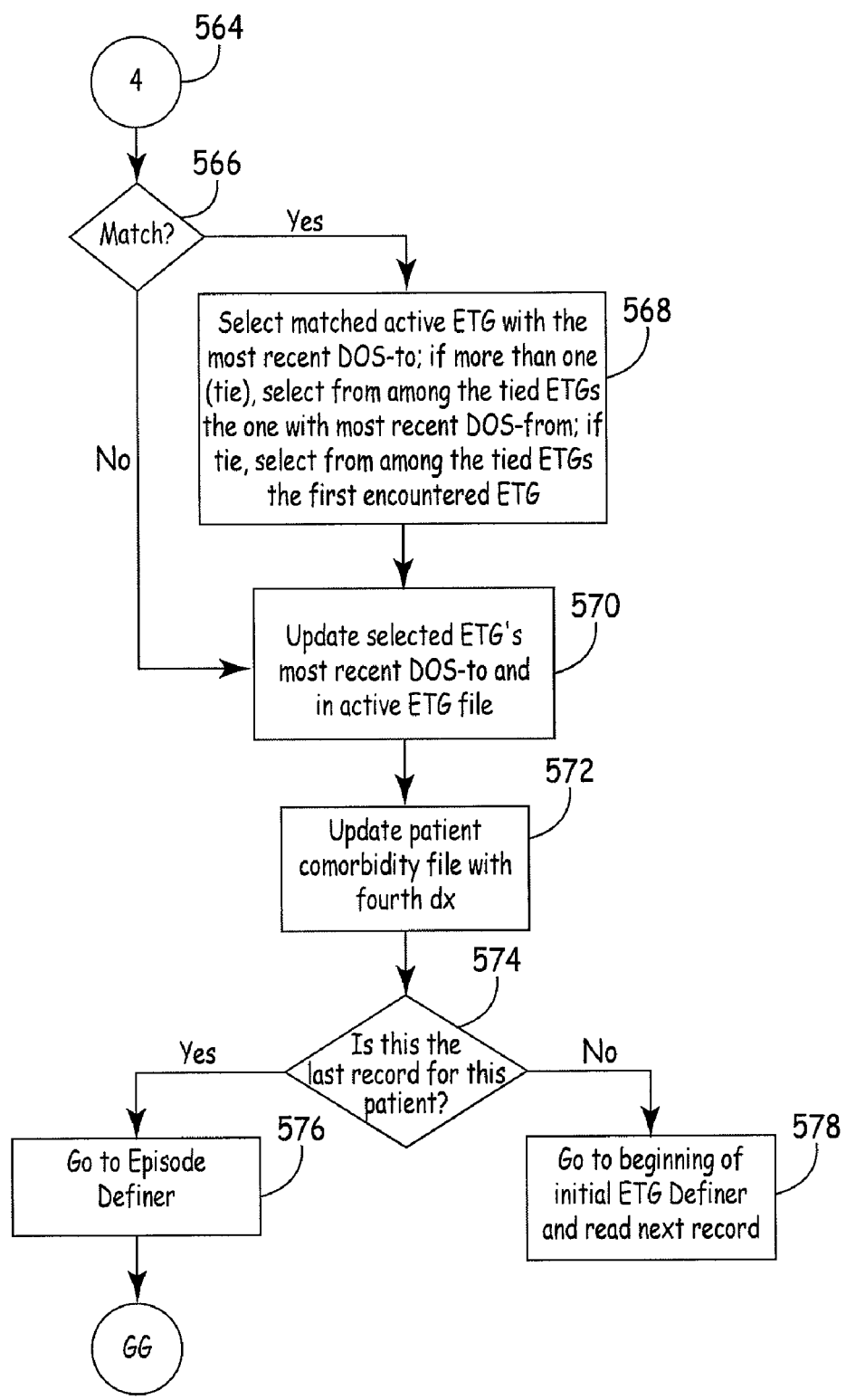
Figure 7A:
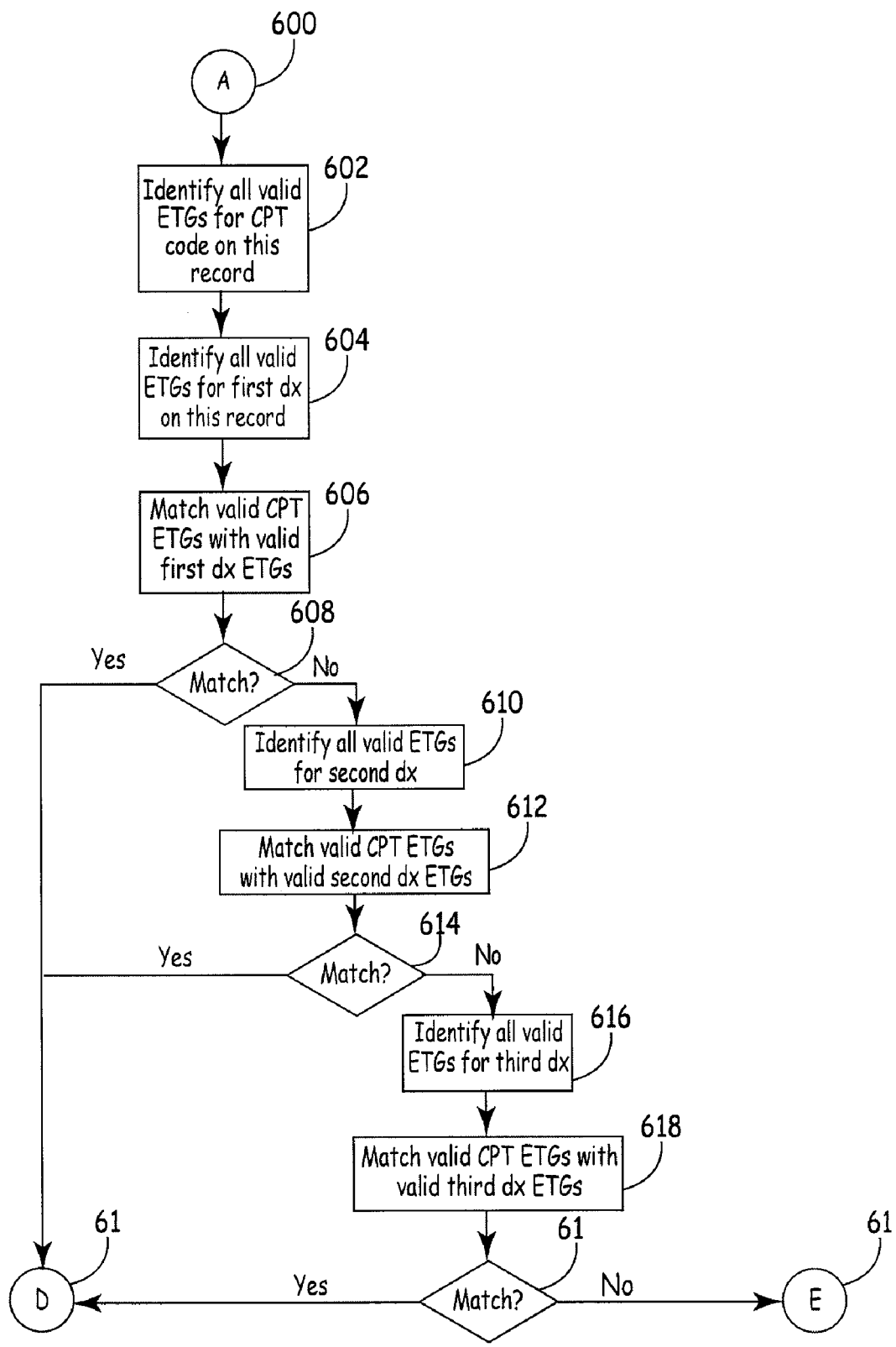
FIGS. 7A-B are flow diagrams illustrating an Ancillary Record Grouping Sub-routine of the ETG Assignor Routine in accordance with the computer-implemented method of the present invention.
Figure 7B:
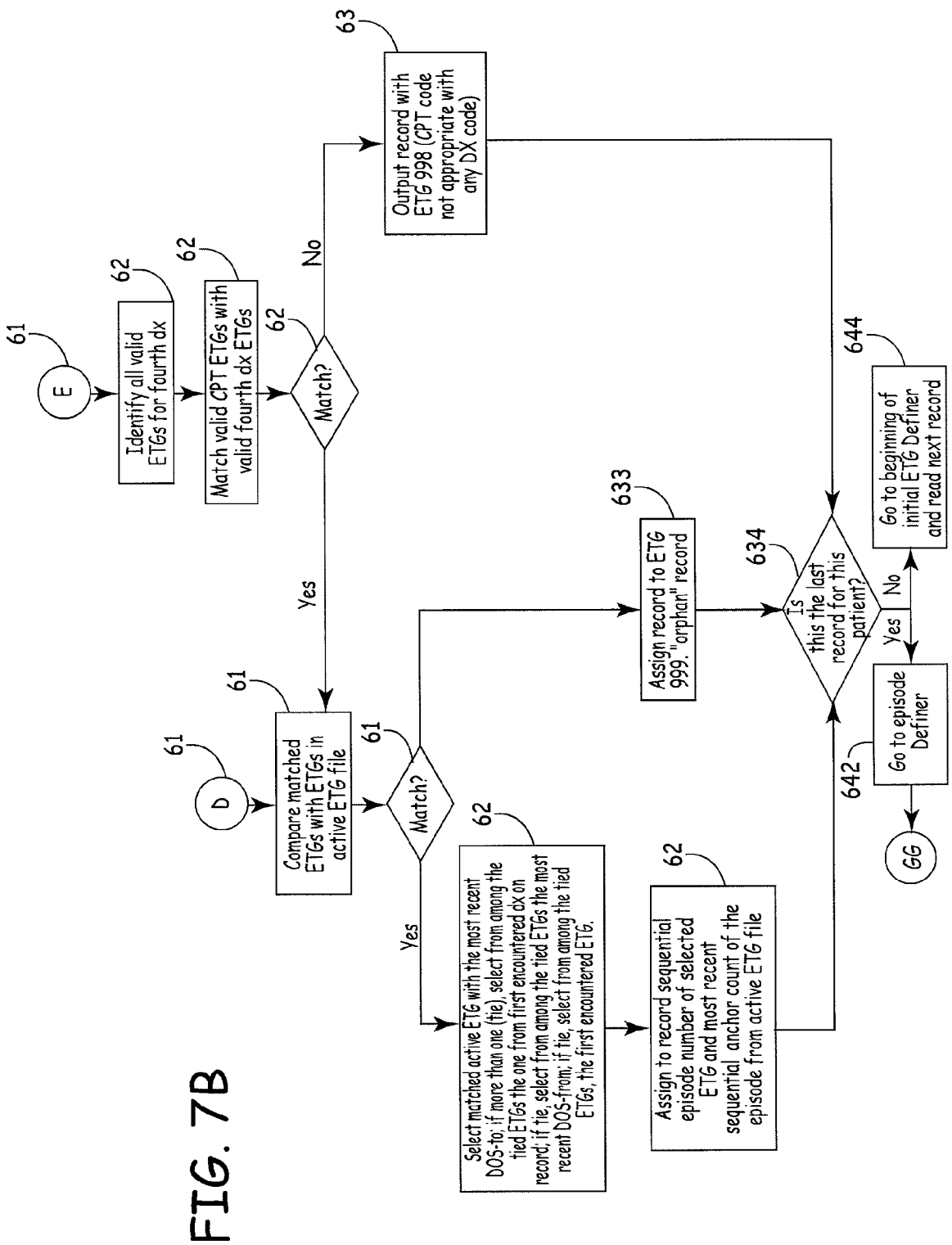
Figure 8A:
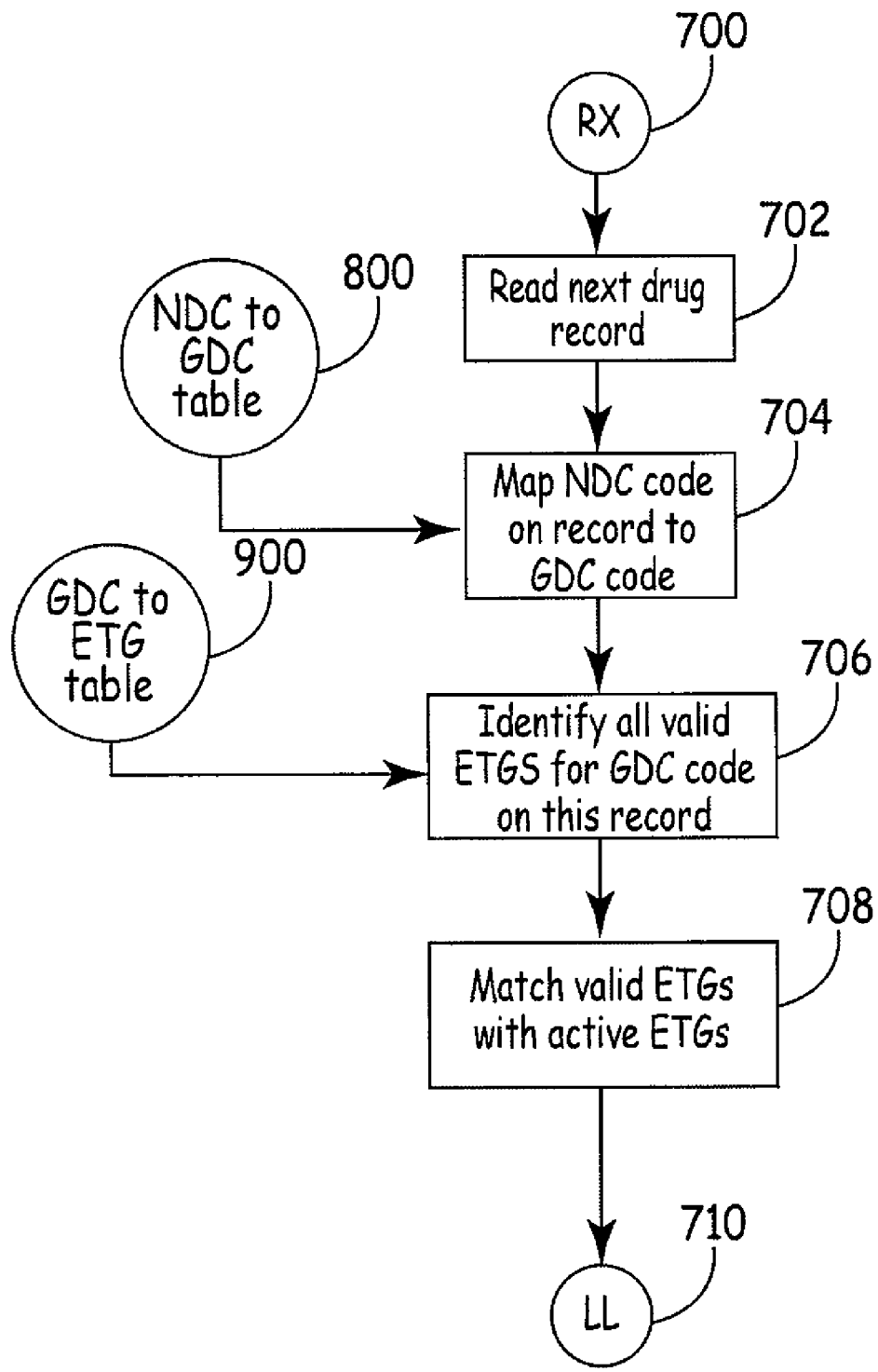
FIGS. 8A-8C are flow diagrams illustrating a Drug Record Grouping Sub-routine of the ETG Assignor Routine in accordance with the computer-implemented method of the present invention.
Figure 8B:
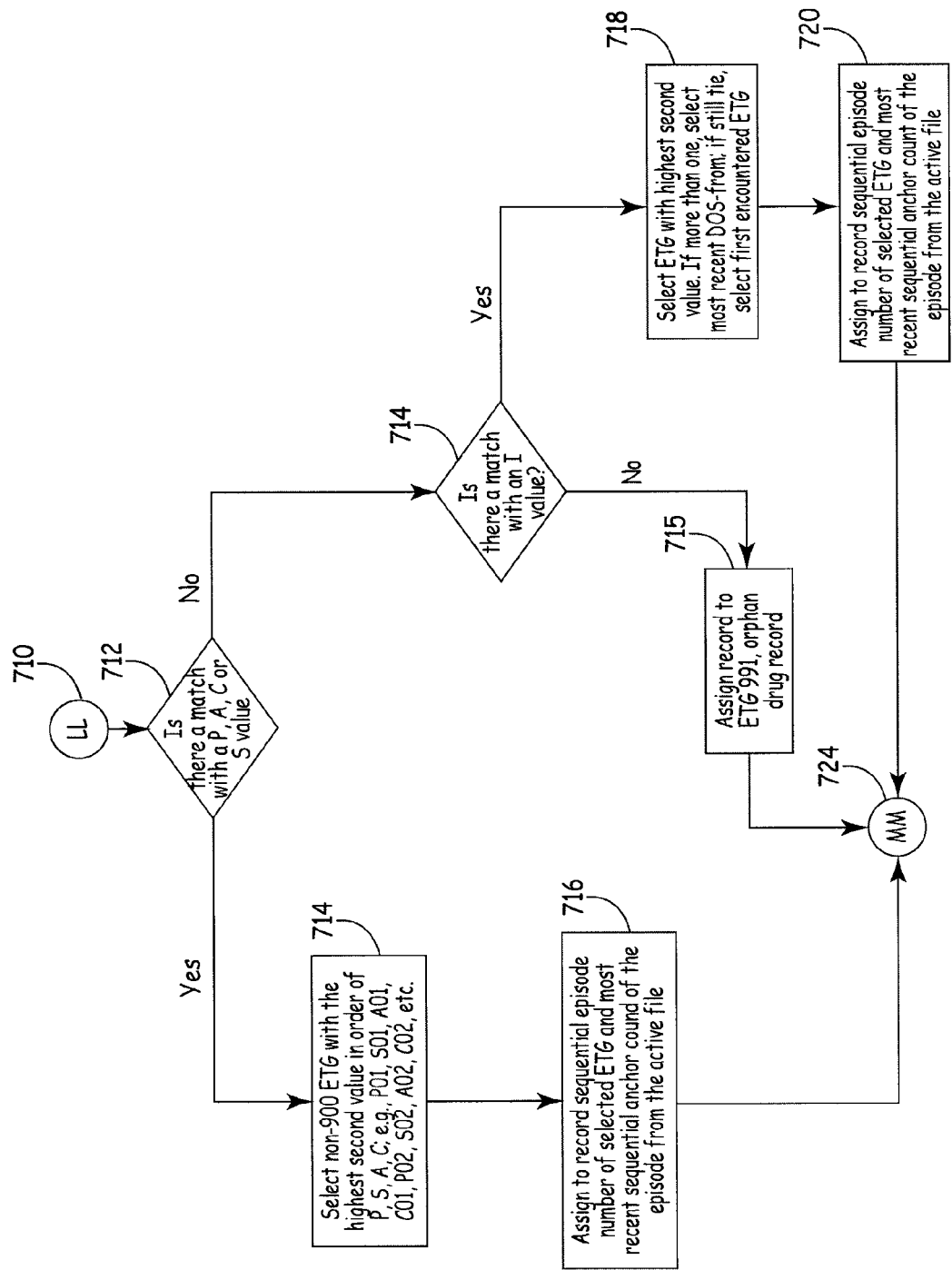
Figure 8C:
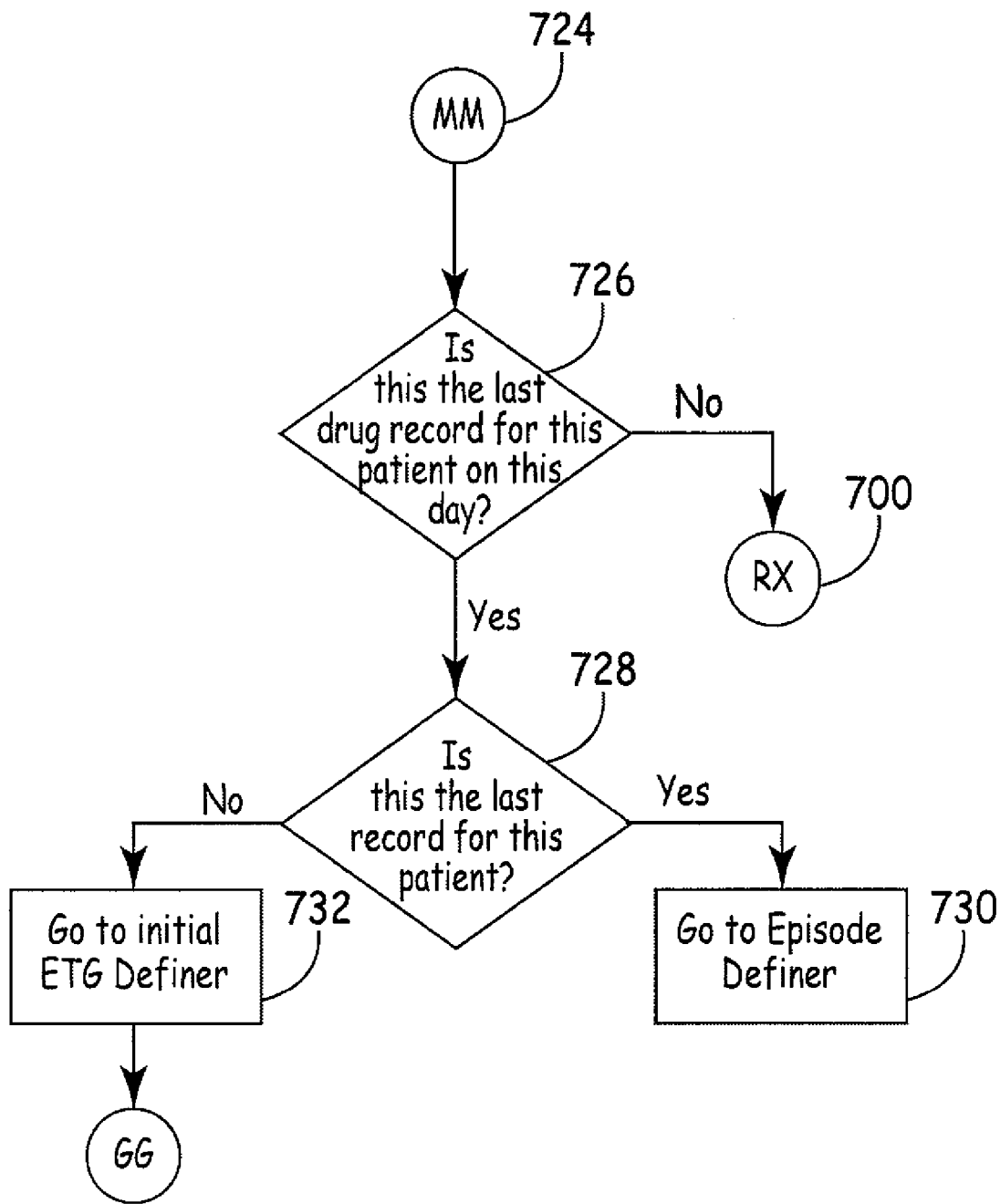

The computer-implemented method of the present invention then initializes an Episode Assignor Routine 200, the operation of which is illustrated in FIGS. 4A-8C. Episode Assignor Routine 200 consists generally of five Sub-routine modules for processing management records, surgery records, facility records, ancillary records and drug records and assigning claims to proper ETGs. FIGS. 4A-4F illustrate initial identification of records as management, surgery, facility ancillary and drug records and the Management Record Grouping Sub-Routine. FIGS. 5A-5E illustrate operation of the Surgery Record Grouping routine 400 for matching surgery claim records to proper ETGs. FIGS. 6A-6E illustrate operation of the Facility Record Grouping routine 500 for matching facilities records to proper ETGs. FIGS. 7A-7B illustrate operation of the Ancillary Record Grouping routine 600 for matching ancillary records to proper ETGs. Finally, FIGS. 8A-8C illustrate operation of the Drug Records Grouping routine 700 for matching drug records to proper ETGs.

Management Records

The Episode Assignor routine begins by executing a Management Records Grouping Sub-routine 200, illustrated in FIGS. 4A-4F, first reads the input claim record for a given patient in step 202. The first processing of the input claim record entails categorizing the record as a management, surgery, facility, ancillary or drug record at step 204. A series of logical operands 208, 210, 212 and 214, read the record and determine whether the record is a management record at step 204, a surgery record at step 208, a facility record at step 210, an ancillary record at step 212 or a drug record at step 214. If an affirmative response is returned in response to logical operand 204, grouping of the management record to an ETG is initialized and processing of the management record proceeds to step 215. If, however, a negative response is returned in response to the logical operand 206, logical operand 208 is executed to determine whether the record is a surgery record. If an affirmative response is returned from logical operand 208, the Surgery Record Grouping routine 400 is initialized. If, however, a negative response to logical operand 208 is returned, logical operand 210 is executed to determine whether the record is a facility record. If an affirmative response is returned in response to logical operand 210, the Facility Record Grouping Sub-routine 500 is executed. If, however, a negative response is returned in response to the logical operand 210, logical operand 212 is executed to determine whether the record is an ancillary record. If an affirmative response is returned from logical operand 212, the Ancillary Record Grouping Sub-routine 600 is executed. If, however, a negative response to logical operand 212 is returned, logical operand 214 is executed to determine whether the record is a facility record. At this point all records except drug records have been selected. Thus, all the remaining records are drug records and the Drug Record Grouping Sub-routine 700 is executed.

Returning now to the initialization of the Management Record Grouping routine 200, and in particular to step 215. Once the record has been categorized as a management record in step 206, the DOS-to value is compared to active episodes for the patient to determine if any active episodes should be closed. Closed episodes are moved to an archive created on the storage means, such as a hard disk or CD-ROM.

The management record is examined and the first diagnosis code on record is read, a diagnosis code (dx) by ETG table 201 is read from the storage means and all valid ETGs for the first diagnosis code on record are identified at step 216. The dx by ETG table 201 consists of a table matrix having diagnosis codes on a first table axis and ETG numbers on a second table axis. At intersection cells of the dx by ETG table are provided table values which serve as operational flags for the inventive method. In accordance with the preferred embodiment of the invention, dx by ETG table values are assigned as follows:

P=primary, with only one P value existing per ETG;
S=shift;
I=incidental;
A=shift to ETG with C value; and
C=P, where P' is a shiftable primary value.

An illustrative example of a section of a dx by ETG table is found at FIG. 11.

ETG validation in step 216 occurs where for a given diagnosis code on record, the code has either a P, S, I, A or C dx-ETG table value. The ETGs identified as valid for the first diagnosis code on record in step 216, are then matched with active open ETGs in step 217 by comparing the valid ETGs with the open ETGs identified in step 215. A logical operand is then executed at step 218 to determine whether a match exists between the valid ETG from the management record and any open ETGs. A negative response at step 218 causes execution of another logical operand at step 220 to determine whether for the first diagnosis code is the P value in the dx-ETG table equal to the ETG for non-specific diagnosis, i.e., ETG 900. If an affirmative response is returned at step 216, ETG identifiers for the second to the fourth diagnosis codes in the management record are established from the dx-ETG table and the ETG identifier value is matched to active specific ETGs in step 222 and execution of the program continues as represented by designator AA 236 bridging to FIG. 5B. If, however, a negative response is returned from logical operand 220, a value of one is added to the management record or anchor count and to the episode count and the ETG with a P value on the dx-ETG table is selected and a new episode is initialized. Further processing of the new episode by the program continues as represented by designator F 236 bridging to FIG. 5C.

If an affirmative response is returned at logical operand step 218, the matched active ETG with the most recent DOS-to are selected at step 230. If a tie is found based upon most recent DOS-to values, then the most recent DOS-from value is selected for matching with active ETGs. If a tie is found at most recent DOS-from values is found, the first encountered ETG is selected and matched. A value of one is then added to the management record or anchor record counter at step 232 and further processing continues as represented by designator G 238 bridging to FIG. 5C.

Figure 4A:
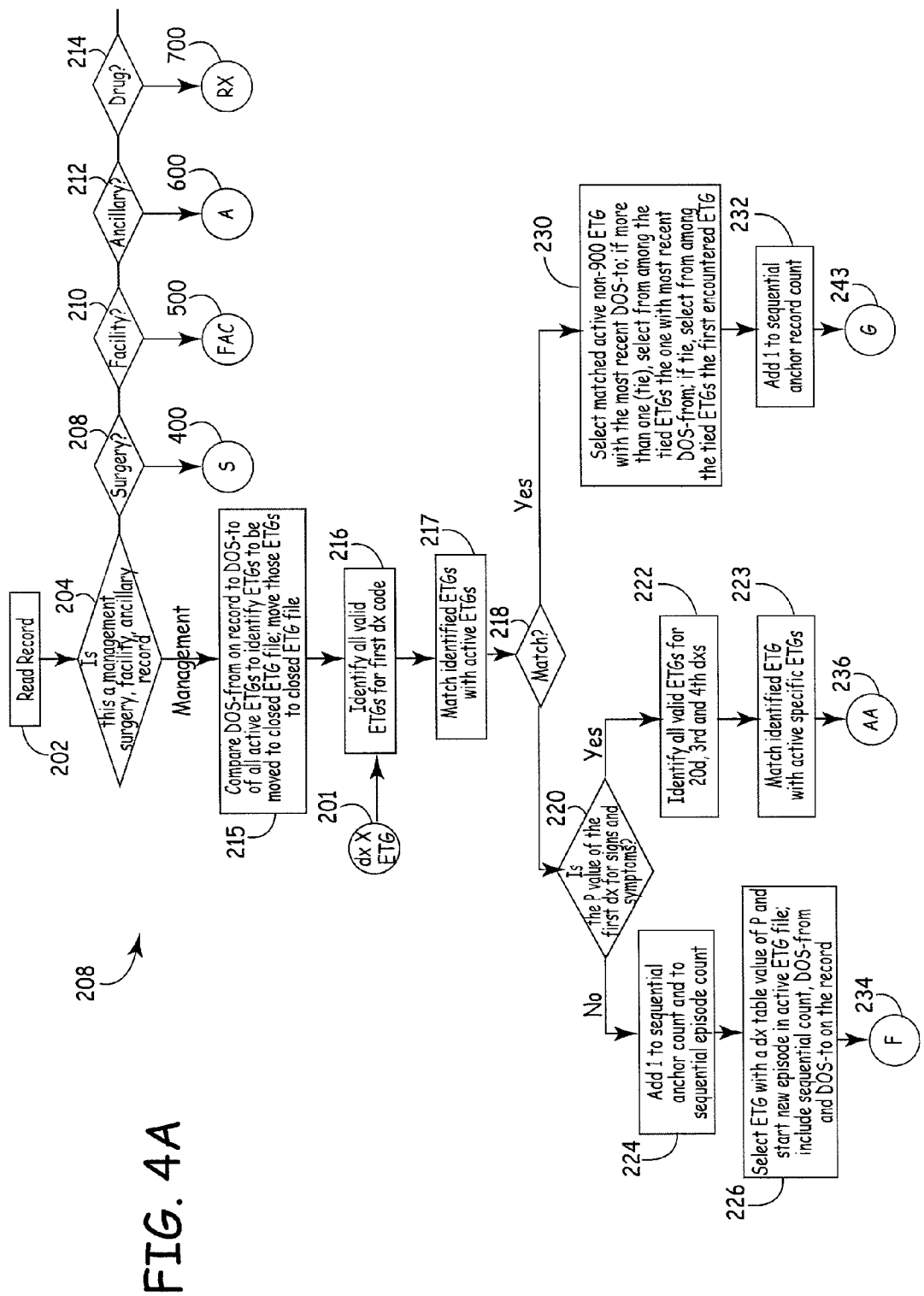

Turning now to FIG. 4B, which is a continuation from designator AA 236 of FIG. 4A, identifier ETGs for the second to fourth diagnoses in the management record are matched to active ETGs in logical operand 237. If an affirmative response is returned in response to logical operand 237, the matched active ETG with the most recent DOS-to is selected in step 240. If there is a tie between two or more ETGs with the most recent DOS-to value, the most recent DOS-from ETG is selected. If, however, there is a tie between two or more active ETGs with the most recent DOS-from value, then the first encountered ETG is selected in step 240. A value of one is then added to the sequential anchor record counter in step 241 and operation of the computer-implemented method continues as indicated by designator G 243 bridging to FIG. 5C.

From logical step 237, if a negative response is returned, the ETG with the second diagnosis value of P is selected at step 242, then a logical query is made to determine whether the selected ETG is a non-specific ETG, i.e., ETG 900 at step 244. A negative response to logical query 244 causes a value of one to be added to the sequential anchor count and to the sequential episode count at step 254. If an affirmative response to logical query 244 is returned, logical queries 246 and 248 are sequentially executed to select ETGs with the third and fourth diagnosis values of P from the dx-ETG table written on the storage means, respectively, and logical query 244 is executed to determine whether the selected ETG is the non-specific ETG, i.e., ETG 900. If a negative response is returned to logical query 244 for the ETG selected in step 248, a value of one is added to the sequential anchor count and to the sequential episode count in step 254. If an affirmative response is returned from logical query 244, a value of one is added to the sequential anchor count and the sequential episode count at step 250.

From step 250, the non-specific ETG, i.e., ETG 900 is selected and a new episode is started in the active ETG file. The updated sequential episode number, the updated sequential anchor count, the DOS-from and the DOS-to from the record are written to the new episode in the active ETG file in step 252.

From step 254, the ETG with a dx-ETG table value of P is selected and a new episode is started in the active ETG file. The updated sequential episode number, the updated sequential anchor count, the DOS-from and the DOS-to from the record are written to the new episode in the active ETG file in step 256. A comorbidity file written on the storage means is then updated with all the dx codes in the management record in step 258.

From each of steps 252 and steps 258 a check is made to determine whether the processed management record is the last record for the patient at logical step 260. An affirmative response returned to logical step 260 prompts the program operation to the Episode Definer Sub-routine 264, bridging to FIG. 9 with identifier GG, while a negative response to logical step 260 returns program operation to the beginning of the ETG Assignor routine 200 and the next patient record is read at step 262.

Figure 4C:
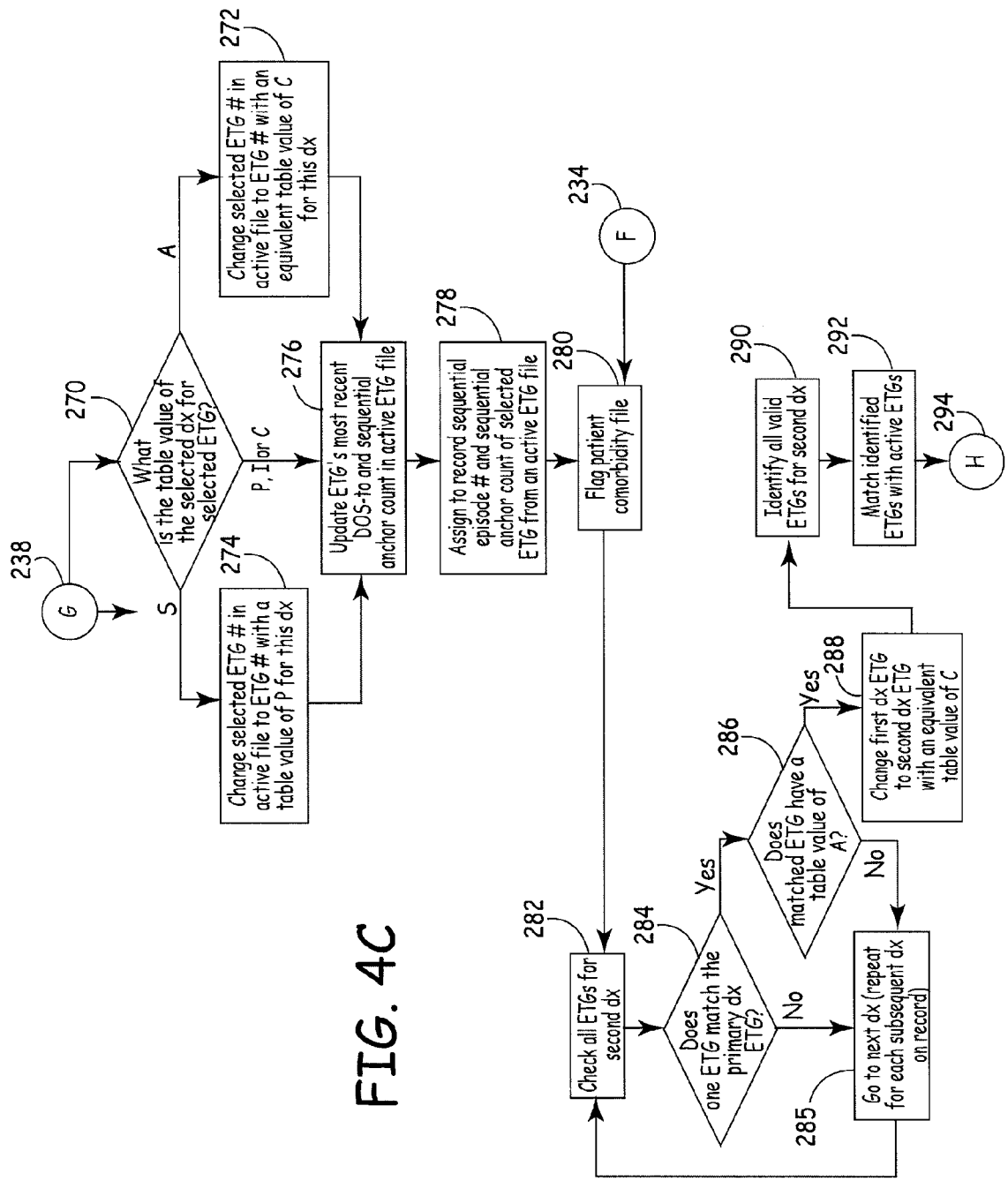

Turning now to FIG. 4C, the bridge reference G 238 is continued from FIG. 4A. For those records having a match with an open ETG, a query is made at step 270 of the dx-ETG table 201 to determine the table value of the dx code for the selected ETG. Again, valid table values are one of P, S, I, A, or C. If the table value returned from step 270 is A, the selected ETG in the active file is changed at step 272 to the ETG number having an equivalent table value of C for the diagnosis on record. If the table value returned from step 270 is S, the selected ETG in the active file is shifted at step 274 to an ETG value having a table value of P for the diagnosis code on record. If the table value is one of P, I or C, the ETG remains the same and the selected active ETG's most recent DOS-to is updated by writing the record date to the ETG DOS-to field, and the sequential anchor count in the selected active ETG is updated to reflect writing of the record to the ETG at step 276.

At step 278, the record is then written with a sequential episode number and the sequential anchor count of the selected ETG from the selected active ETG. In this manner, the record is identified with the ETG and the specific episode. The patient's co-morbidity file is flagged with the output read from bridge designator F at step 234. A patient's comorbidity file is a predefined list of diagnoses which have been identified as comorbidities. If during the course of grouping a patient's records, a management record is encountered which is a comorbidity diagnosis, the ETG for that diagnosis is flagged or "turned on" in the comorbidity file. Then, during the execution of the Episode Definer Routine, all the patient's episodes with an ETG which can shift based on the presence of a comorbidity and which are "turned on" are appropriately shifted to the ETG "with comorbidity".

A loop beginning at step 282 is then executed to determine whether the ETG assigned by the first diagnosis code should be shifted to another ETG based upon the second, third and fourth diagnoses on record. At step 282, the second diagnosis is read from the patient's claim record and all valid ETGs for the second diagnosis are read from the dx-ETG table 201. A logical operand 284 is executed to determine whether one of the valid ETGs for the second diagnosis matches the primary diagnosis ETG. If a negative response is returned to logical operand 284, a loop back at step 285 is executed to step 282 for the next sequential diagnosis code on record, i.e., the third and forth diagnosis codes on record. If an affirmative response is returned to the logical operand 284, the a logical operand 286 queries the table value of the matched ETG to determine if a value of A is returned from the dx-ETG table. If a negative response is returned, the loop back step 285 is initialized. If an affirmative response is returned, the first dx ETG is flagged for change to a second dx ETG having an equivalent table value of C for the second diagnosis code on record at step 288 and all valid ETGs for the current diagnosis code on record are identified at step 290 from the dx-ETG table. The identified C-value ETG is then matched with any open active ETGs at step 292. Program operation then continues at bridge H 292 to FIG. 4D.

Figure 4D:
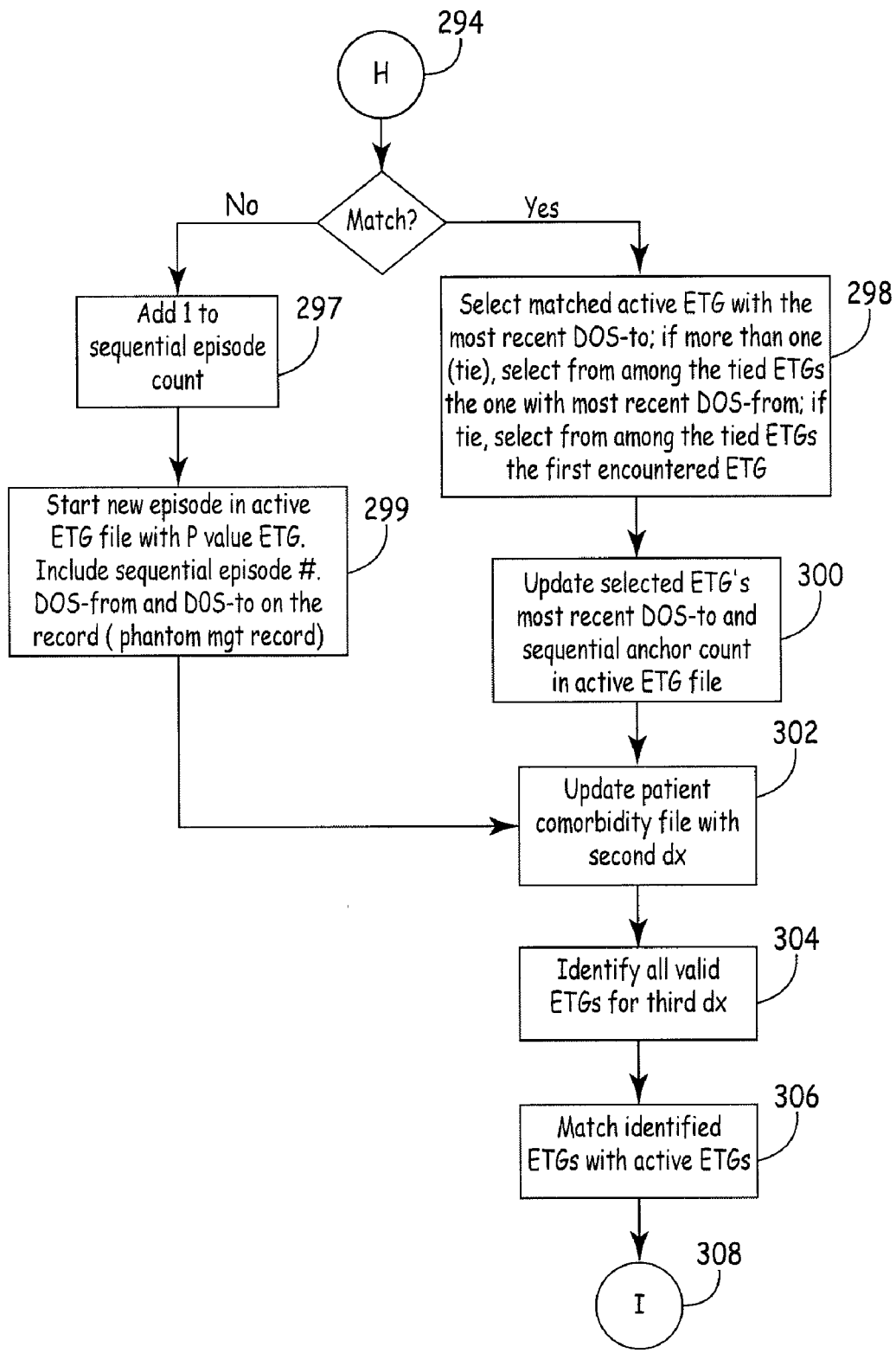

At FIG. 4D the continued operation of the Management Grouping Sub-routine from bridge H 292 of FIG. 4C. Logical operand 296 queries the open active ETGs to determine whether a valid match with the identified C-value ETG exists. If a negative response is returned to logical operand 296, a value of 1 is added to the sequential episode count at step 297 and a new episode having a P value ETG is started in the patient's master active ETG file at step 299. The new episode is written with a sequential episode number, DOS-from and DOS-to values and forms a phantom management record. A phantom record is an anchor record, management or surgery, with more than one diagnosis, which is assigned to one episode and its corresponding ETG based on one diagnosis, but can start a new episode(s) or update the most recent date of another active episode(s) based on other diagnoses on the record.

If an affirmative response is returned from logical operand 296, the matched active ETG with the most recent DOS-to value is selected at step 298. If a tie is found based upon most recent DOS-to values, then the most recent DOS-from value is selected for matching with active ETGs. If a tie is found at most recent DOS-from values is found, the first encountered ETG is selected and matched. The selected ETG's most recent DOS-to and sequential anchor count are updated in the patient's master active ETG file in step 300.

For either the new episode created at step 299 or the updated ETG from step 300, the patient's co-morbidity file is then updated with the second diagnosis code on-record at step 302. Processing then continues to identify all valid ETGs for a third diagnosis code on record at step 304 and the identified valid ETGs from step 304 are compared to the active ETGs in the patient's master active ETG file in step 306.

Figure 4E:
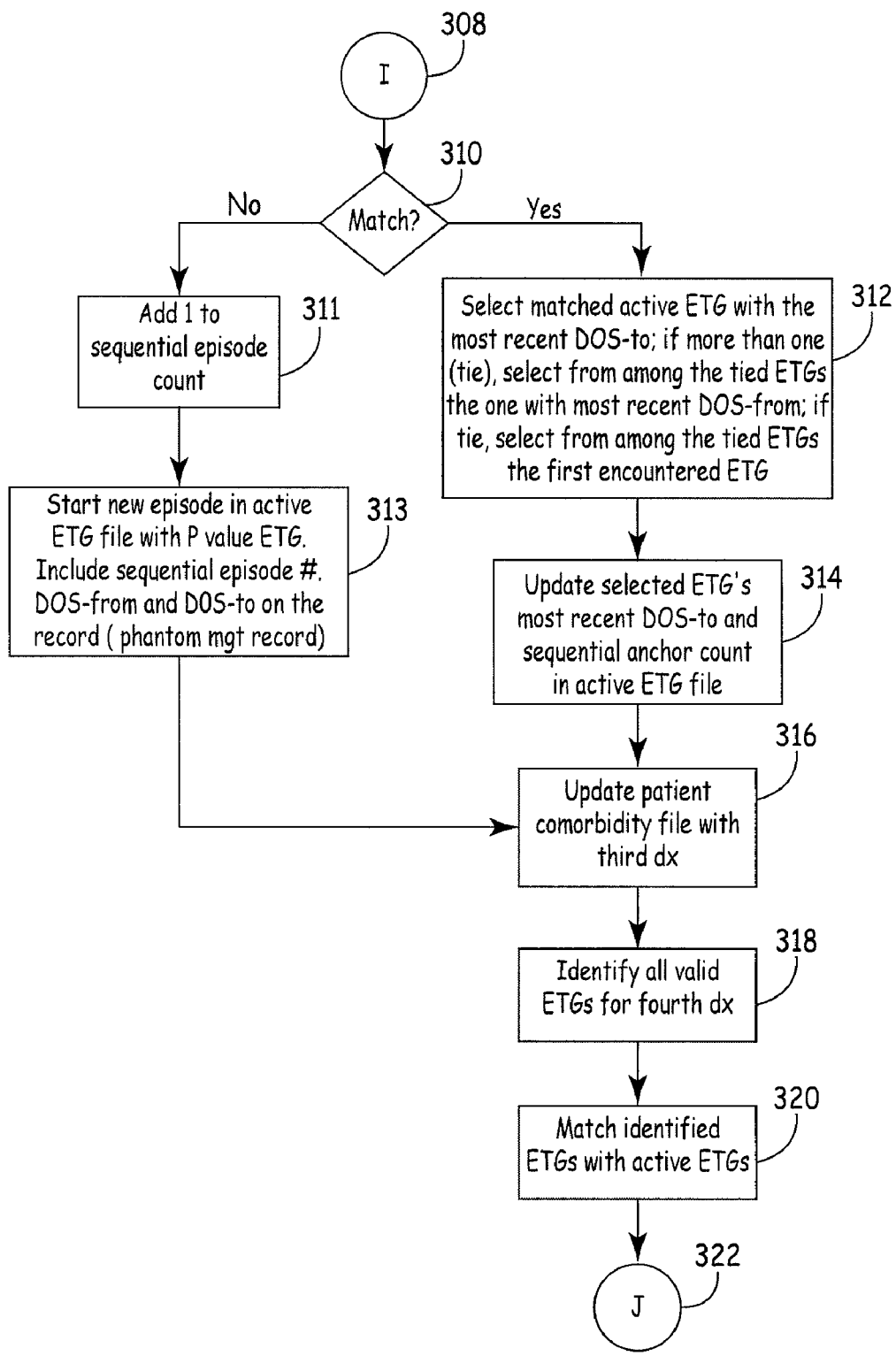

Bridge 1308 continues to FIG. 4E, and a logical operand 310 is executed to query the patient's master active ETG file to determine whether a match exists between the valid ETGs identified in step 304 with any active ETG from the patients master active ETG file. If a negative response is returned to logical operand 310, a value of 1 is added to the sequential episode count at step 311 and a new episode having a P value ETG is started in the patient's master active ETG file at step 313. The new episode is written with a sequential episode number, DOS-from and DOS-to values and forms a phantom management record.

If an affirmative response is returned from logical operand 310, the matched active ETG with the most recent DOS-to value is selected at step 312. Again a decisional hierarchy is executed. If a tie is found based upon most recent DOS-to values, then the most recent DOS-from value is selected for matching with active ETGs. If a tie is found at most recent DOS-from values is found, the first encountered ETG is selected and matched. The selected ETG's most recent DOS-to and sequential anchor count are updated in the patient's master active ETG file in step 314.

For either the new episode created at step 311 or the updated ETG from step 314, the patient's co-morbidity file is then updated with the third diagnosis code on-record at step 316. Processing then continues to identify all valid ETGs for a fourth diagnosis code on record at step 318 and the identified valid ETGs from step 3318 are compared to the active ETGs in the patient's master active ETG file in step 320. Bridge reference I 322, bridges to FIG. 4F.

Figure 4F:
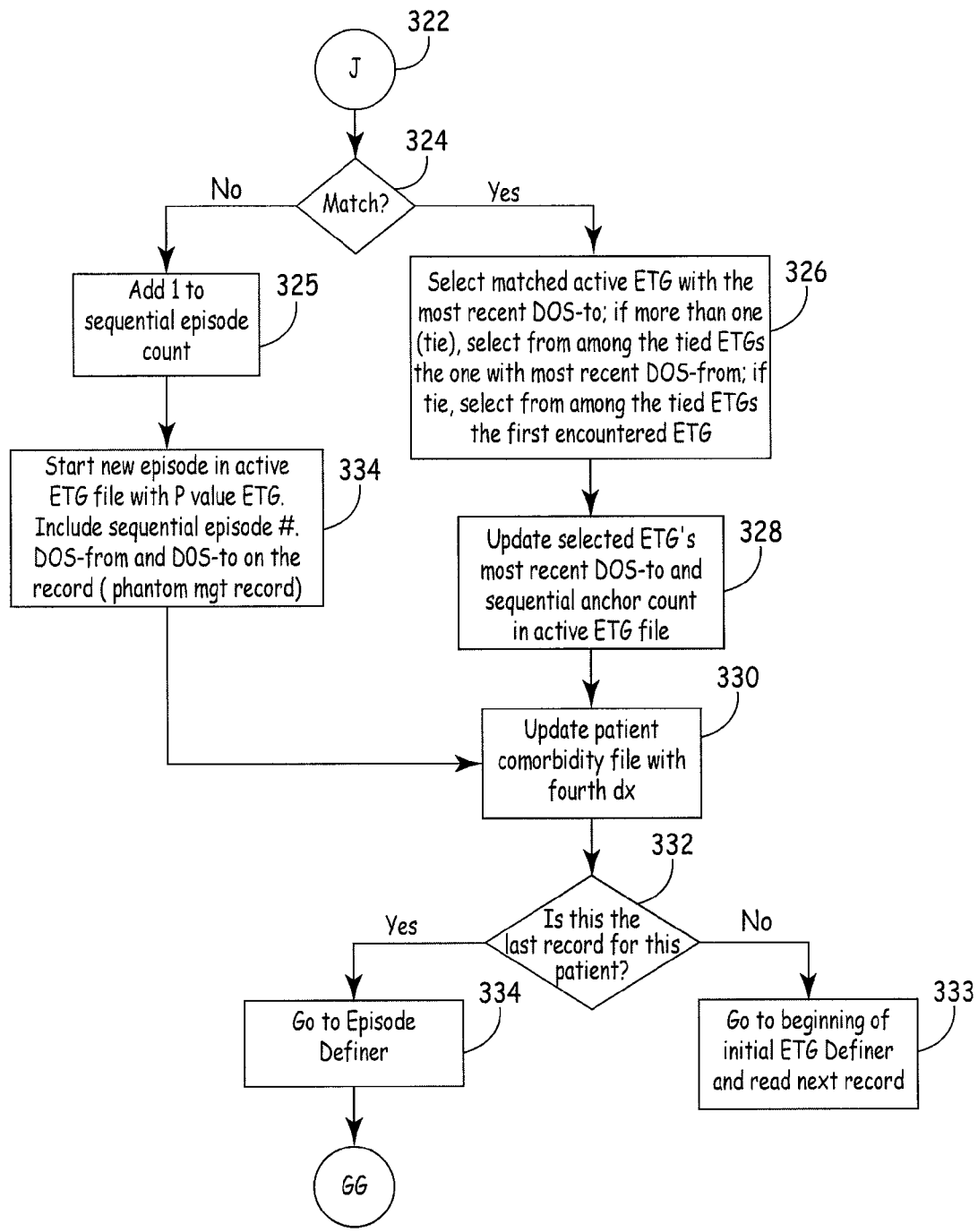

Turning to FIG. 4F, a logical operand 324 is executed to query the patient's master active ETG file to determine whether a match exists between the valid ETGs identified in step 320 with any active ETG from the patients master active ETG file. If a negative response is returned to logical operand 324, a value of 1 is added to the sequential episode count at step 325 and a new episode having a P value ETG is started in the patient's master active ETG file at step 337. The new episode is written with a sequential episode number, DOS-from and DOS-to values and forms a phantom management record.

If an affirmative response is returned from logical operand 324, the matched active ETG with the most recent DOS-to value is selected at step 326. Again a decisional hierarchy is executed. If a tie is found based upon most recent DOS-to values, then the most recent DOS-from value is selected for matching with active ETGs. If a tie is found at most recent DOS-from values is found, the first encountered ETG is selected and matched. The selected ETG's most recent DOS-to and sequential anchor count are updated in the patient's master active ETG file in step 328.

For either the new episode created at step 337 or the updated ETG from step 324, the patient's co-morbidity file is then updated with the fourth diagnosis code on-record at step 330. A check is then made to determine whether the processed record is the last record for the patient by execution of logical operand 332 and reading the input claim records from the storage means. If logical operand 332 returns an affirmative value, the ETG Definer Sub-routine is called at step 334, as represented by bridge reference GG. If, however, a negative response is returned to logical operand 332, program execution returns to the step 204 of the Episode Assignor routine 200 and the next patient claim record is read from the storage means.

Surgery Records

Grouping of Surgery Records to ETGs is governed by the Surgery Record Grouping Sub-routine 400, the operation of which is illustrated in FIGS. 5A-5D.

For those patient claim records identified as Surgery Records at step 208, the DOS-from value on-record is compared with the DOS-to value read from the patient master active ETG file at step 402. This identifies and flags those active ETGs which are to be closed, the flagged ETGs are then moved to the patient master closed ETG file. The first diagnosis code on-record is then read and compared to the dx-ETG table 201 to identify all possible valid ETGs for the first diagnosis code on-record in step 404.

Surgery records are coded with treatment codes (CPT codes). Each surgery record has a single CPT code value. The CPT code on-record is then read, and compared to a CPT by ETG table 401 previously written to the storage means. The CPT-ETG table will have pre-determined table values. For example, in accordance with the preferred embodiment of the invention, the CPT-ETG table 401 has table values of R, W and X, where R is a value shiftable to W and X is a validator value. All valid ETGs for the on-record CPT code are identified by this comparison at step 406. A logical operand 408 is then executed to determine whether there is a match of valid ETGs returned from the dx-ETG table 201 and the CPT-ETG table 401. If an affirmative response is returned to logical operand 408, a second logical operand 410 is executed to determine whether a match of valid specific ETGs exists. Again, if an affirmative response is returned from second logical operand 410, the valid specific ETGs matched in step 410 are then compared at step 414 with the open active ETGs for the patient read from the patient's master active ETG file at step 412. If an affirmative response is returned from step 414, the matched ETG with the most recent DOS-to is selected at step 416 and a value of 1 is added to the sequential anchor count in the selected ETG at step 418. In step 416, if a tie is found based upon most recent DOS-to values, then a decisional hierarchy is followed to select the most recent DOS-from value for matching with active ETGs. If a tie is found at most recent DOS-from values is found, the first encountered ETG is selected and matched.

If a negative response is returned to any of logical operands 408, 410 or 414, second, third and fourth dx codes on-record are read and all possible valid ETGs are read in step 411 from the dx-ETG table 201. Further processing of the valid ETGs output from step 411 is continued at FIG. 5B identified by bridge reference P, 413.

Figure 5A:
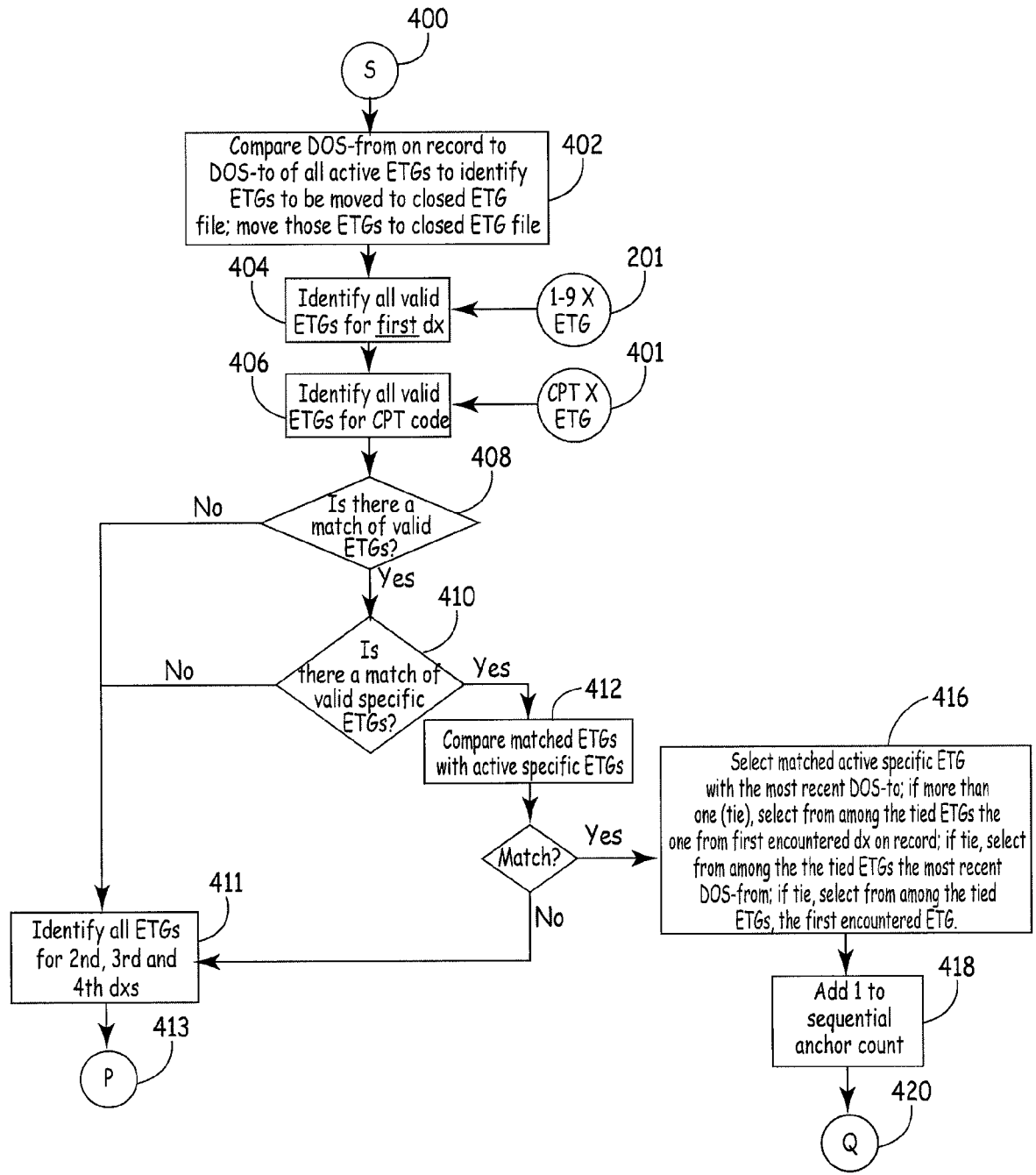
FIGS. 5A-5D are flow diagrams illustrating a Surgery Record Grouping Sub-routine of the ETG Assignor Routine in accordance with the computer-implemented method of the present invention.
Figure 5B:
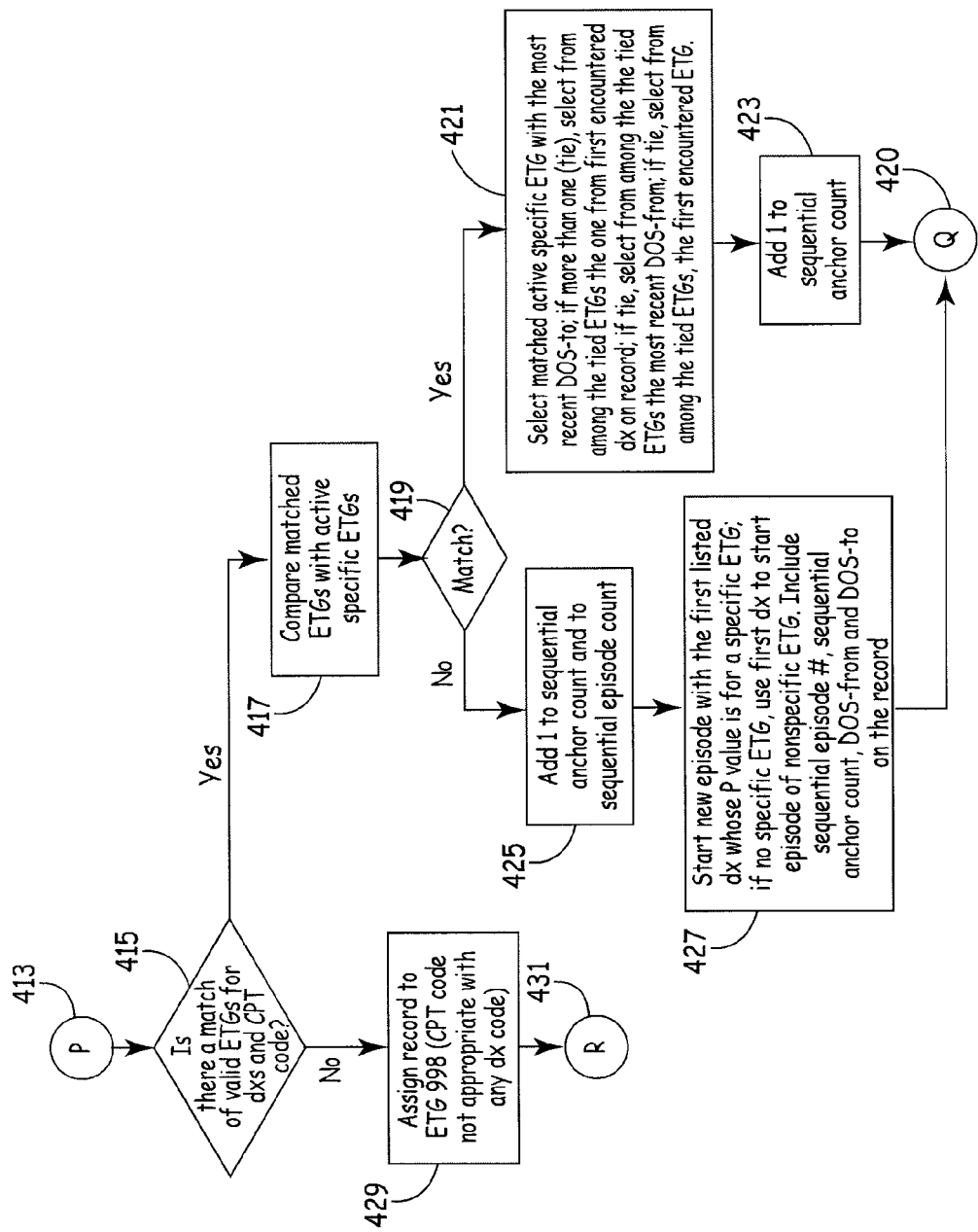

Turning to FIG. 5B, a logical operand 415 compares the valid ETGs for the second, third and fourth dx codes with the valid ETGs for the CPT code on-record in step 411. If a negative response is returned from logical operand 415, the patient claim record is assigned to an ETG reserved for match errors between dx code and CPT code, e.g., ETG 998, and further processing of the match error ETG bridges at reference R, 431, to FIG. 5D.

If an affirmative response is returned from logical operand 415, the matched ETGs are compared with active ETGs read from the patient master active ETG file at step 417 and logical operand 419 is executed at step 419 to determine whether any valid matches between matched ETGs and active ETGs. If a negative response is returned to logical operand 419, a value of 1 is added to the sequential anchor count and to the sequential episode count at step 425 and a new episode is started at step 437 with the first dx code on-record having a P value for a specific ETG in the dx-ETG table 201. If no specific ETG has a P value, a non-specific ETG having a P value for the dx code on record is used to start the new episode. The new episode is started by writing the sequential episode number, the sequential anchor count, the DOS-from and the DOS-to values on the record.

If an affirmative response is returned from logical operand 419, the matched specific ETG with the most recent DOS-to is selected at step 421. If a tie is found based upon most recent DOS-to values, then the most recent DOS-from value is selected for matching with active ETGs. If a tie is found at most recent DOS-from values is found, the first encountered ETG is selected and matched. A value of 1 is added to the sequential anchor count at step 423. Processing the new episode started at step 427 or of the selected matched specific ETG at step 421 continues to bridge Q, 420, continued at FIG. 5C.

Figure 5C:
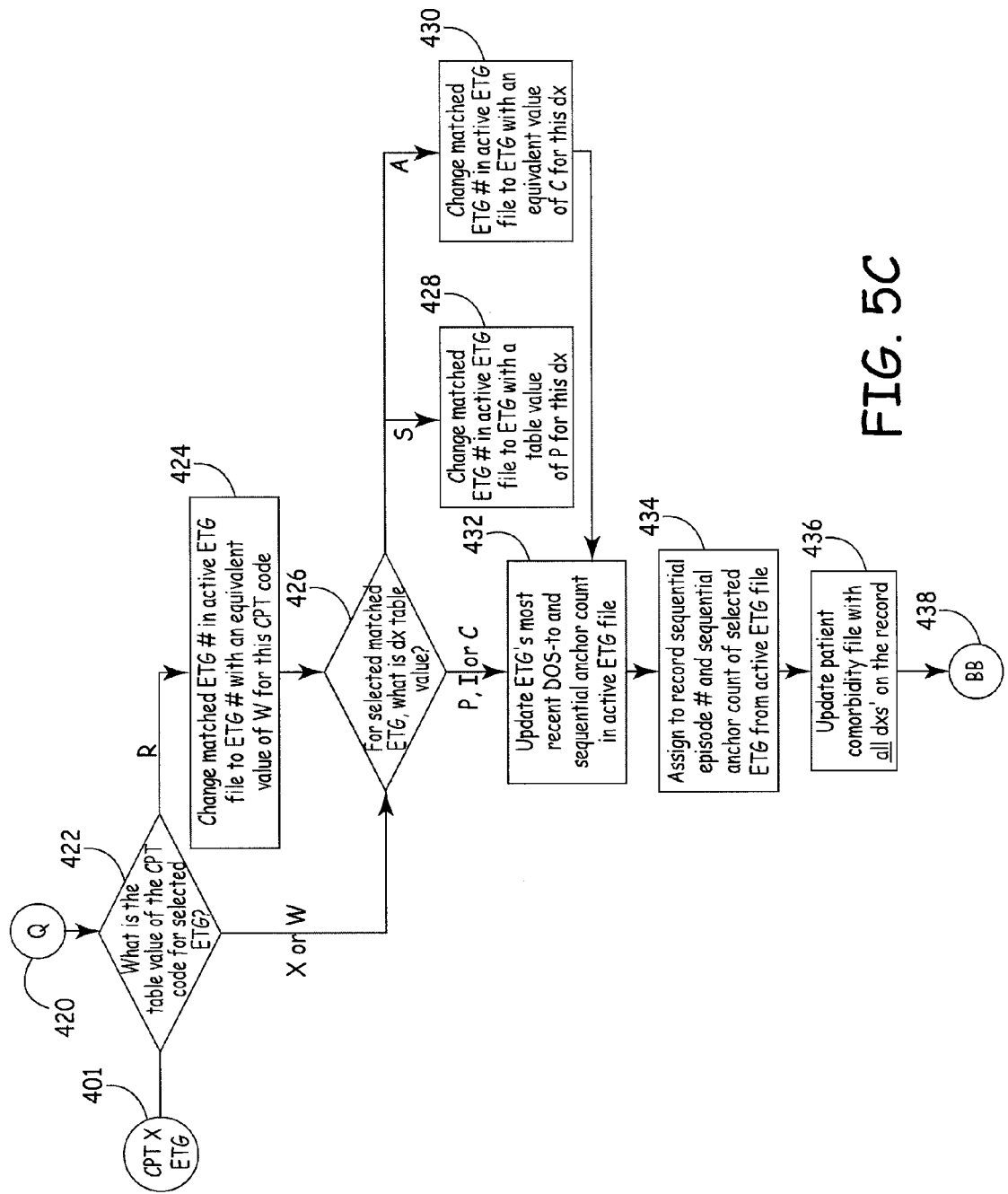

Turning to FIG. 5C, bridged from reference Q, 420, logical operand 422 is executed which reads the CPT-ETG table 401 and determines the table value of the selected ETG from step 421 and step 427 based on the CPT value on-record. If a table value of R is returned from the read of the CPT-ETG table 401 at step 422, the matched ETG in the master active ETG file is shifted at step 424 to the ETG with an equivalent value of W for the CPT code on-record. If a table value of X or W is returned from step 422 or from step 242, the dx-ETG table 201 is read at step 426 and the dx code for the selected matched ETG from the CPT-ETG table 401 or the shifted ETG from step 424 is read. From the dx-ETG table 201, if a value of S is returned, the matched ETG in the patient master active ETG file is shifted at step 428 to the ETG with a table value of P for the dx code on-record. If a table value of A is returned, the matched ETG in the patient master active ETG file is changed in step 430 to an equivalent value of C for the dx code on-record. If a table value of P, I or C is returned either from logical operand 426, or from the ETG change step 428 or the ETG shift step 430, the DOS-to and the sequential anchor count of the ETG in the patient master active ETG file are updated in step 432. The patient claim record is then assigned and written with the sequential episode number and the sequential anchor count of the selected ETG at step 434. The patient co-morbidity file is then updated with all diagnosis codes on-record at step 436.

Figure 5D:
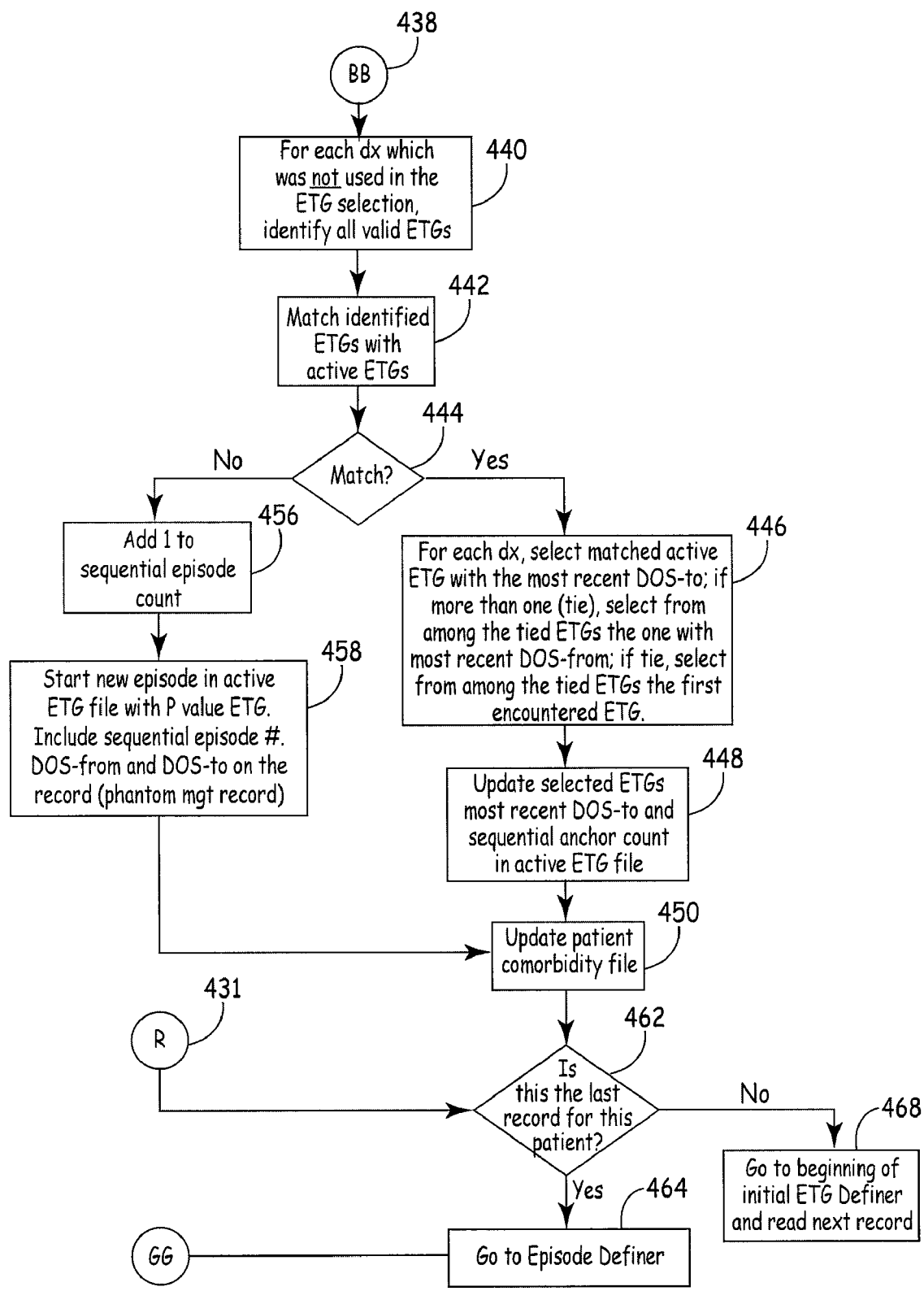

FIG. 5D bridges from FIG. 5C with bridge reference BB, 438. In FIG. 5D, the diagnosis codes on-record which were not used in the ETG selection described above, are then read from the patient claim record to identify all possible valid ETGs in the dx-ETG table 201. The identified possible valid ETGs are then matched against the patient master active ETG file in step 442 and logical operand 444 is executed to validate the matches. If an affirmative response is returned to logical operand 444, for each matched dx code on-record, the matched active ETG with the most recent DOS-to is selected at step 446. If a tie is found based upon most recent DOS-to values, then the most recent DOS-from value is selected for matching with active ETGs. If a tie is found at most recent DOS-from values is found, the first encountered ETG is selected and matched. The selected ETG's most recent DOS-to value is updated to the date of the patient medical claim, and the sequential anchor count in the active ETG is updated in step 448.

If a negative response is returned to logical operand 444, a value of 1 is added to sequential episode count at step 456 and a new episode having a P value ETG is started in the patient's master active ETG file at step 458. The new episode is written with a sequential episode number, DOS-from and DOS-to values and forms a phantom surgery record. If an affirmative response is returned to logical operand 444, the matched active ETG for each diagnosis code is selected at step 446 on the basis of the most recent DOS-to value. If a tie is found based upon most recent DOS-to values, then the most recent DOS-from value is selected for matching with active ETGs. If a tie is found at most recent. DOS-from values is found, the first encountered ETG is selected and matched. The DOS-to field of the selected ETG from step 446 is updated in step 448 to the date of service on-record and the sequential anchor count in the active ETG file is updated. From either step 458 or from step 448, the patient co-morbidity file is updated to reference the selected ETG and a check is made to determine whether the patient claim record processed in step 429, which assigned an invalid dx-CPT code match to the record, or from step 450, which updated the co-morbidity file, is the last record for the patient at logical operand 462. If an affirmative response is returned to logical operand 462, record processing proceeds to the Episode Definer Sub-routine at step 464, bridged by reference GG, to FIG. 9. If, however, a negative response is returned to logical operand 462, a loop back 468 to the beginning of the ETG Assigner routine 200 is executed and the next patient claim record is read.

Facility Records

The Facility Record Grouping Sub-routine 500 assigns facility records to ETGs on the basis of diagnosis codes on-record. The patient claim record is read and the first diagnosis code on-record is read to the dx-ETG table 201 to identify all valid ETGs for the first dx code at step 502. The identified valid ETGs are then compared to the open active ETGs in the patient master active ETG file in step 504. Logical operand 506 executes to determine whether any valid matches exist between identified ETGs for the dx code and the active ETGs for the patient. If a negative response is returned to step 506, a value of 1 is added to the sequential episode count at step 507 and a new episode is started in step 509 in the patient active ETG file with the ETG corresponding to the dx-ETG table value of P. If logical operand 507 returns an affirmative response, a query of the matched ETG value is made at step 508 to determine whether the matched ETG has a table value of P, C, A or S. If a negative response is returned to step 508, the matched active ETG with the most recent DOS-from value is selected at step 511. If a tie is found based upon most recent DOS-to values, then the most recent DOS-from value is selected for matching with active ETGs. If a tie is found at most recent DOS-from values is found, the first encountered ETG is selected and matched. If an affirmative response is returned at step 508, the table value of the matched ETG table value is identified at step 510. If the table value for the matched ETG in the dx-ETG table 201 is S, the matched ETG is shifted at step 514 to the ETG having a table value of P for the dx code. If the table value for the matched ETG returns a value of A, the matched ETG in the patient master active ETG file is changed at step 512 to an ETG having an equivalent table value of C for the dx code. If a table value of either P or C is returned at step 510, the most recent DOS-to is updated at step 516 in the ETG to the on-record claim date. Further processing of the claim record from steps 509, 511 and 516 bridges at reference 1, 520, to FIG. 6B.

Turning to FIG. 6B, bridged from reference 1, 520, in FIG. 6A, the patient's co-morbidity file is updated with the first dx code at step 522. A loop beginning at step 524 is then executed to determine whether the ETG assigned by the first diagnosis code should be shifted to another ETG based upon the second, third and fourth diagnoses on record. At step 524, the second diagnosis is read from the patient's claim record and all valid ETGs for the second diagnosis are read from the dx-ETG table 201. A logical operand 526 is executed to determine whether one of the valid ETGs for the second diagnosis matches the primary diagnosis ETG. If a negative response is returned to logical operand 526, a loop back at step 527 is executed to step 524 for the next sequential diagnosis code on record, i.e., the third and forth diagnosis codes on record. If an affirmative response is returned to the logical operand 524, the logical operand 528 queries the table value of the matched ETG to determine if a value of A is returned from the dx-ETG table. If a negative response is returned, the loop back step 527 is initialized. If an affirmative response is returned, the first dx ETG is flagged for change to a second dx ETG having an equivalent table value of C for the second diagnosis code on record at step 530. All valid ETGs for the second diagnosis code on record are identified at step 532 from the dx-ETG table. The identified ETGs are then matched with any open active ETGs at step 532. Program operation then continues at bridge 2, 536 to FIG. 6C.

At FIG. 6C the continued operation of the Facility Record Grouping Sub-routine 500 from bridge 2 of FIG. 6b is illustrated. Logical operand 538 queries the open active ETGs to determine whether a valid match with the identified ETGs exists. If a negative response is returned to logical operand 538, the patient co-morbidity file is updated with the second diagnosis code at step 544. If an affirmative response is returned from logical operand 538, the matched active ETG with the most recent DOS-to value is selected at step 540. If a tie is found based upon most recent DOS-to values, then the most recent DOS-from value is selected for matching with active ETGs. If a tie is found at most recent DOS-from values is found, the first encountered ETG is selected and matched. The selected ETG's most recent DOS-to and sequential anchor count are updated in the patient's master active ETG file in step 542.

Processing then continues to identify all valid ETGs for a third diagnosis code on record at step 546 and the identified valid ETGs from step 546 are compared to the active ETGs in the patient's master active ETG file in step 548.

Bridge 3, 550, continues to FIG. 6D, and a logical operand 552 is executed to query the patient's master active ETG file to determine whether a match exists between the valid ETGs identified in step 548 with any active ETG from the patients master active ETG file. If a negative response is returned to logical operand 538, the patient's comorbidity file is updated with the third diagnosis code at step 558.

If an affirmative response is returned from logical operand 552, the matched active ETG with the most recent DOS-to value is selected at step 554. Again a decisional hierarchy is executed. If a tie is found based upon most recent DOS-to values, then the most recent DOS-from value is selected for matching with active ETGs. If a tie is found at most recent DOS-from values is found, the first encountered ETG is selected and matched.

The patient's co-morbidity file is then updated with the third diagnosis code on-record at step 558. Processing then continues to identify all valid ETGs for a fourth diagnosis code on record at step 560 and the identified valid ETGs from step 3318 are compared to the active ETGs in the patient's master active ETG file in step 562. Bridge reference 4, 564, bridges to FIG. 6D.

Turning to FIG. 6D, a logical operand 566 is executed to query the patient's master active ETG file to determine whether a match exists between the valid ETGs identified in step 562 with any active ETG from the patients master active ETG file. If a negative response is returned to logical operand 566, the patient's comorbidity file is updated with the fourth diagnosis code.

If an affirmative response is returned from logical operand 566, the matched active ETG with the most recent DOS-to value is selected at step 568. In the event of a tie, a decisional hierarchy is executed. If a tie is found based upon most recent DOS-to values, then the most recent DOS-from value is selected for matching with active ETGs. If a tie is found at most recent DOS-from values is found, the first encountered ETG is selected and matched. The selected ETG's most recent DOS-to are updated in the patient's master active ETG file in step 570 and the patient's co-morbidity file is then updated with the fourth diagnosis code on-record at step 572. A check is then made to determine whether the processed record is the last record for the patient by execution of logical operand 574 and reading the input claim records from the storage means. If logical operand 574 returns an affirmative value, the ETG Definer Sub-routine is called at step 576, as represented by bridge reference GG. If, however, a negative response is returned to logical operand 574, program execution returns to the step 204 of the Episode Assignor routine 200 and the next patient claim record is read from the storage means at step 578.

Ancillary Records

Operation of the Ancillary Record Grouping Sub-routine 600 is illustrated in FIGS. 7A-7B. Like surgery records, ancillary records are grouped to ETGs on the basis of both dx codes and CPT code on record. First all valid ETGs for the treatment or CPT code on-record are identified in step 602 from the CPT-ETG table 401. Then all valid ETGs for the first dx code on record are identified in step 604 from the dx-ETG table 201. The ETGs from the CPT-ETG table 401 are then compared at step 606 to the ETGs from the dx-ETG table 201 and a logical operand 608 determines whether there is an ETG match. An affirmative response returned from logical operand 608 continues record processing at bridge D, 610, which continues on FIG. 7B. A negative response returned from logical operand 608 prompts a look up on the dx-ETG table to determine all valid ETGs for the second diagnosis code on record in step 611. Step 613 again compares the valid ETGs for the CPT code on record and with the valid ETGs for the second dx code on record and a logical operand 614 is executed to match the second dx code ETG with the CPT code ETG. Again, an affirmative response returned from logical operand 614 continues record processing at bridge D, 610, which continues on FIG. 7B. If a negative response is returned to logical operand 614, a look up on the dx-ETG table occurs to determine all valid ETGs for the third diagnosis code on record in step 615. Step 616 again compares the valid ETGs for the CPT code on record and with the valid ETGs for the third dx code on-record, which bridges E, 619, to FIG. 7B for identification of all valid ETGs for the fourth dx code on-record at step 625.

Step 627 then compares the valid ETGs for the CPT code on record and with the valid ETGs for the fourth dx code on record and a logical operand 629 is executed to match the fourth dx code ETG with the CPT code ETG. An affirmative response returned from logical operand 629 continues to step 616 which compares the matched ETGs with the ETGs in the patient master active ETG file and a query is made at logical operand 618 to determine whether any valid matches exist. If a negative response is returned to logical operand 629, the record is output to the ETG reserved for a CPT code-dx code mismatch at step 631 and a check is made at step 635 to determine whether the record is the last record for the patient.

If a match is found between the matched ETGs from the dx code-CPT code comparison in step 616. The matched active ETG with the most recent DOS-to value is selected. In the event of a tie, a decisional hierarchy is executed. If a tie is found based upon most recent DOS-to values, then the most recent DOS-from value is selected for matching with active ETGs. If a tie is found at most recent DOS-from values is found, the first encountered ETG is selected. The sequential episode number of the selected ETG is assigned to the record and the most recent sequential anchor count of the episode from the active ETG file is assigned to the record at step 622.

If the response to logical operand 618 is negative, the record is assigned to an orphan record ETG at step 633 and maintained in the claims records until subsequent record processing either matches the record to an ETG or the orphan record DOS-from exceeds a one-year time period, at which time the record is output to an error log file.

A check is then made to determine whether this record is the last record for the patient at step 635. If logical operand 635 returns an affirmative value, the ETG Definer Sub-routine is called at step 642, as represented by bridge reference GG. If, however, a negative response is returned to logical operand 635, program execution returns to the step 204 of the Episode Assignor routine 200 and the next patient claim record is read from the storage means at step 644.

Prescription Drug Records

FIGS. 8A-8C illustrate the operation of the Drug Record Grouping Sub-routine 700. Drug Record Grouping Sub-routine 700 references two predetermined tables previously written to the storage means. The first of the tables is a National Drug Code (NDC) by Generic Drug Code (GDC) table 800. This table acts as a translator table to translate a large number of NDCs to a smaller set of GDCs. A second pre-defined table is employed and is constructed as a GDC by ETG table 900. The GDC by ETG table is used, in conjunction with the NDC by GDC translator table, to identify all valid ETGs for a particular NDC code in the claim record.

Once identified as a drug record in the initial operation of the Episode Assignor Routine 200, the drug record is read from storage to memory in step 702. The NDC code on-record is converted to a GDC code by reading from the NDC-GDC table 800 in step 704. Using the GDC number so identified, all possible valid ETGs for the GDC code are identified in step 706. The possible valid ETGs for the GDC code are then compared to the patient master active ETG file in step 708. Following bridge LL, 710, to FIG. 8B, a logical operand is executed in step 712 based upon the comparison executed in step 708, to determine whether a match occurs having a table value of P, A, C or S.

If a negative response is returned to logical operand 712, a check is made to determine whether a match having table value I in the GDC-ETG table 900 exists in step 713. If another negative response is returned to logical operand 713, the record is flagged an orphan drug record and assigned to an orphan drug record ETG in step 715. If an affirmative response is returned to logical operand 713, the ETG with the highest second value is selected in step 718 (e.g. I1, I2, I3 and so on). If more than one ETG having the highest second value exists, the ETG having the most recent DOS-from value is selected. If a tie is again encountered, the first encountered ETG is selected. A sequential episode number and the most recent sequential anchor count of the episode from the patient master active ETG file is assigned to the drug record for the selected ETG in step 720.

If an affirmative response is returned to logical operand 712, the ETG having the highest second value, in order of P, S, A, C is selected in step 714 (e.g. P1, then P2 . . . then S1, then S2 . . . and so on). The record is then assigned a sequential episode number of the selected ETG and the most recent sequential anchor count of the episode from the patient master active ETG file in step 716.

Further processing of the drug record continues from steps 716, 715 and 720 through bridge MM, 724 and is described with reference to FIG. 8C. A check is made in step 726 to determine whether the drug record is the last drug record for the patient on the record date. If a negative response is returned, a loop back to the top of the Drug Record Grouping Sub-routine 700 is executed. If an affirmative response is returned at step 726, a check is made to determine whether the drug record is the last record for the patient in step 728. If logical operand 728 returns an affirmative value, the ETG Definer Sub-routine is called at step 732, as represented by bridge reference GG. If, however, a negative response is returned to logical operand 728, program execution returns to the step 204 of the Episode Assignor routine 200 and the next patient claim record is read from the storage means at step 730.

Figure 9:
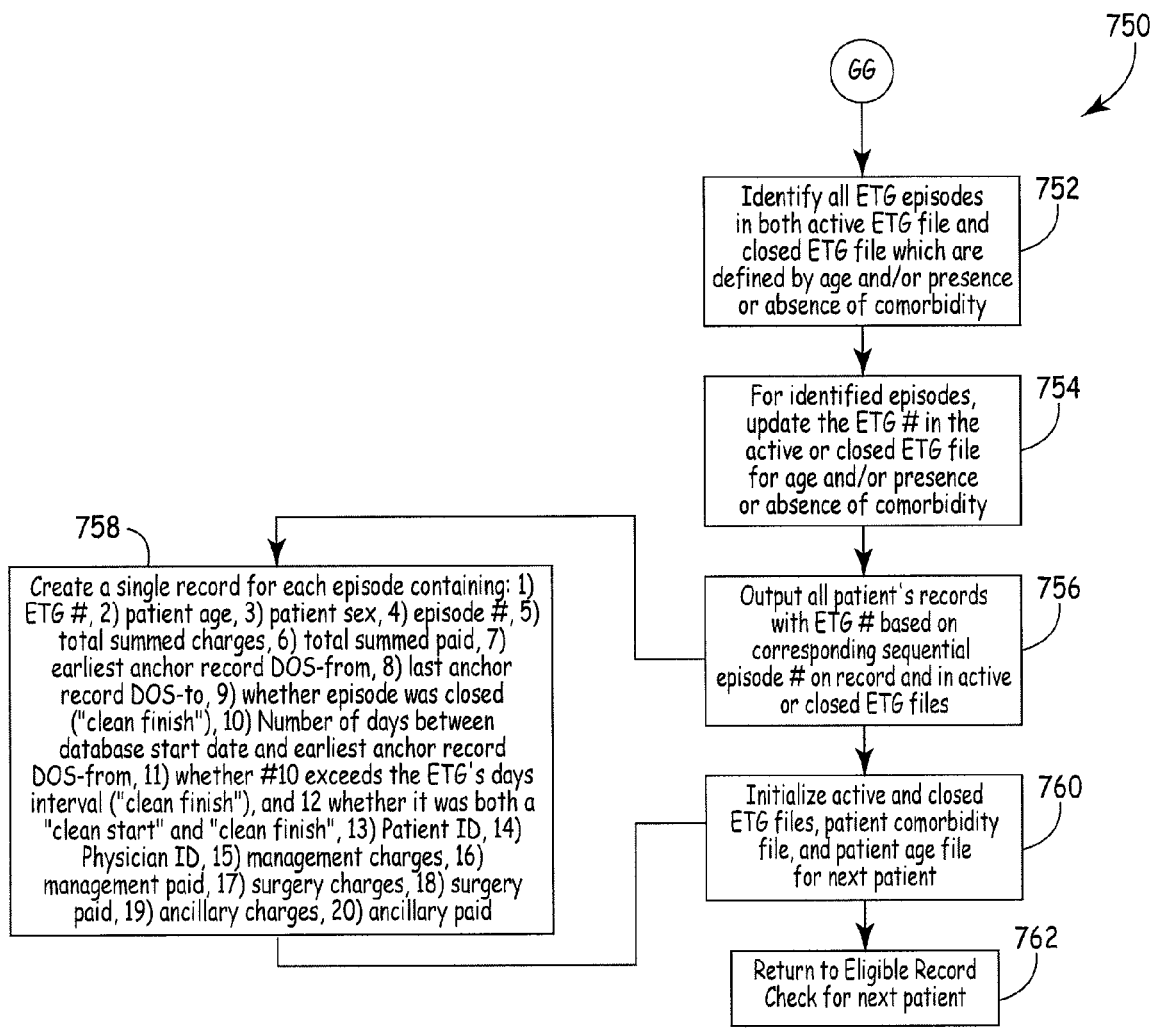
FIG. 9 is a flow diagram illustrating the Episode Definer Routine in accordance with the computer-implemented method of the present invention.

The Episode Definer Sub-routine is illustrated with reference to FIG. 9. Episode Definer Routine 118 is employed to assign all non-specific claims records, i.e., those initially assigned to ETG 900, to specific more appropriate ETGs. Episode Definer routine 750. Once all episodes have been grouped to ETGs, all ETG episodes in both active and closed ETGs are then identified in step 752 by patient age and presence or absence of a comorbidity. The ETG number for each episode is then shifted and re-written to an ETG appropriate for the patient age and/or presence or absence of a comorbidity in step 754. All patient records are then output in step 756 to the display, to a file or to a printer, along with their shifted ETG number, sequential episode number of the record and in patient master active and closed ETG file for the patient. The Episode Definer routine 750 then writes a single record at step 758 for each episode containing key analytical information, for example: the ETG number, patient age, patient sex, the sequential episode number, the total sum charges, the total sum paid, the earliest anchor record DOS-from value, the last anchor record DOS-to value, patient identification, physician identification, management charges, management charges paid, surgery charges, surgery charges paid, ancillary charges, and ancillary charges paid.

After the single record for each episode is written in step 758 for the patient, processing for the next patient begins by initialization of the next patient master active and closed ETG file, the next patient co-morbidity file, and the patient age file in step 760 and the Eligible Record Check Routine is re-initiated for processing claims records for the next patient at step 762.

Example

Figure 10:
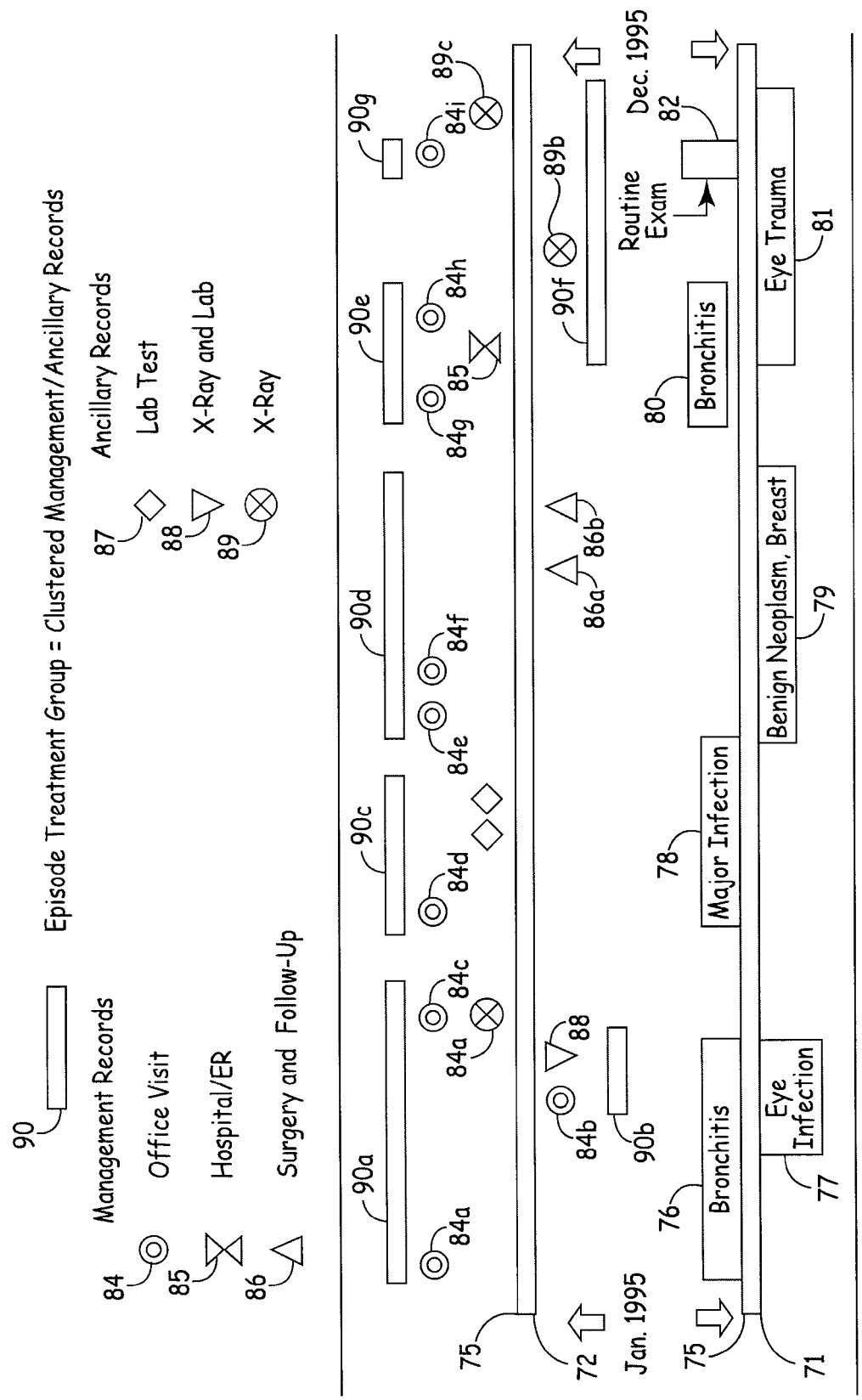
FIG. 10 is diagrammatic timeline illustrating a hypothetical patient diagnosis and medical claims history during a one year period and grouping of claim records as management records and ancillary records with cluster groupings.

FIG. 10 provides an example of Management and Ancillary record clustering over a hypothetical time line for a single patient over a one year period from January, 1995 to December, 1995. FIG. 10 depicts time frames of occurrences for claims classified as management records, i.e., office visit 84, hospital or emergency room visit 85, and surgery and surgical follow-up 86 and for claims records classified as ancillary records, i.e., laboratory tests 87, X-ray and laboratory tests 88 and x-ray 89. Two time lines are provided. A first timeline 71 includes the diagnosis and the time duration of the diagnosed clinical condition. A second timeline 72 includes the claim events which gave rise to the medical claims. Where claim events occur more than once, an alphabetic designator is added to the reference numeral to denote chronological order of the event. For example, the first office visit is denoted 84*a*, the second office visit is denoted 84*b*, the third denoted 84*c*, etc. Vertical broken lines denote the beginning and end of each Episode Treatment Group 90, and facilitate correlation of the episode event, e.g., office visit, with the resulting diagnosis, e.g., bronchitis.

A first office visit 84*a* resulted in a diagnosis of bronchitis 76. Office visit 84*a* started an episode 90*a* for this patient based upon the bronchitis diagnosis 76. A second office visit 84*b* occurred concurrently with the bronchitis episode 90*a*, but resulted in a diagnosis of eye infection 77. Because the eye infection 77 is unrelated to the open bronchitis episode ETG 90*a*, a new eye infection episode ETG 90*b* is started. An X-ray and lab test 88 was taken during the time frame of each of the bronchitis episode 90*a* and the eye infection 90*b*. Based upon the CPT-ETG table, discussed above, the X-ray and lab test 88 is assigned to the eye infection episode 90b. A third office visit 84c and x-ray 89a occurred and related to the bronchitis episode 90a rather than the eye infection episode 90b.

A fourth office visit 84d occurred and resulted in a diagnosis of major infection 78 unrelated to the bronchitis diagnosis 76. Because the major infection 78 is unrelated to the bronchitis, the fourth office visit 84d opened a new ETG 90c. Two subsequent lab tests 87a and 87b were both assigned to the only open episode, i.e., ETG 90c.

A fifth office visit 84e resulted in a diagnosis of benign breast neoplasm 79, which is unrelated to the major infection ETG 90c. A fifth office visit 84e opened a new ETG 90d because the benign breast neoplasm is unrelated to either the bronchitis episode ETG 90a, the eye infection episode ETG 90b, or the major infection episode 90c. Sixth office visit 84f was assigned then to the only open episode, i.e., ETG 90d. Similarly, the surgery and follow-up records 86a and 86b related to the benign neoplasm ETG 90d and are grouped to that ETG.

Some months later, the patient has a seventh office visit 84g which resulted in a diagnosis of bronchitis 80. However, because the time period between the prior bronchitis episode 76 and the current bronchitis episode 80 exceeds a pre-determined period of time in which there was an absence of treatment for bronchitis, the bronchitis episode 90a is closed and the bronchitis episode 90e is opened. A hospital record 85 occurs as a result of an eye trauma and eye trauma 81 is the resulting diagnosis. Because the eye trauma 85 is unrelated to the bronchitis 80, a new eye trauma ETG 90f is started which is open concurrently with the bronchitis ETG 90e. An eighth office visity 84h occurs during the time when both ETG 90e and ETG 90f are open. Eighth office visity 84h is, therefore, grouped to the ETG most relevant to the office visity 84h, i.e., ETG 90e. A subsequent x-ray record 89b occurs and is related to the eye trauma diagnosis and is, therefore, grouped to ETG 90f. Because and absence of treatment has occurred for the bronchitis ETG 90e, that ETG 90e is closed.

Finally, while the eye trauma ETG 90f is open, the patient has a routine office visit 84h which is unrelated to the open ETG 90f for the eye trauma diagnosis 91. Because it is unrelated to the open ETG 90f, the routine office visity 84i starts and groups to a new episode 90g which contains only one management record 84i. An x-ray record 89c occurs after and is unrelated to the routine office visity 84i. The only open episode is the eye trauma episode 90f and the x-ray record 89c is, therefore, grouped to the eye trauma episode 90f. At the end of the year, all open episodes, i.e., the eye trauma ETG 90f are closed.

It will be apparent to those skilled in the art, that the foregoing detailed description of the preferred embodiment of the present invention is representative of a type of health care system within the scope and spirit of the present invention. Further, those skilled in the art will recognize that various changes and modifications may be made without departing from the true spirit and scope of the present invention. Those skilled in the art will recognize that the invention is not limited to the specifics as shown here, but is claimed in any form or modification falling within the scope of the appended claims. For that reason, the scope of the present invention is set forth in the following claims.

TABLE 1

| ETG | DESCRIPTION |
|---|---|
| 1 | AIDS with major infectious complication |
| 2 | AIDS with minor infectious complication |
| 3 | AIDS with inflammatory complication |
| 4 | AIDS with neoplastic complication, with surgery |
| 5 | AIDS with neoplastic complication, w/o surgery |
| 6 | HIV sero-positive without AIDS |
| 7 | Major infectious disease except HIV, with comorbidity |
| 8 | Septicemia, w/o comorbidity |
| 9 | Major infectious disease except HIV and septicemia, w/o comorbidity |
| 10 | Minor infectious disease |
| 11 | Infectious disease signs & symptoms |
| 20 | Diseases of the thyroid gland, with surgery |
| 21 | Hyper-functioning thyroid gland |
| 22 | Hypo-functioning thyroid gland |
| 23 | Non-toxic goiter |
| 24 | Malignant neoplasm of the thyroid gland |
| 25 | Benign neoplasm of the thyroid gland |
| 26 | Other diseases of the thyroid gland |
| 27 | Insulin dependent diabetes, with comorbidity |
| 28 | Insulin dependent diabetes, w/o comorbidity |
| 29 | Non-insulin dependent diabetes, with comorbidity |
| 30 | Non-insulin dependent diabetes, w/o comorbidity |
| 31 | Malignant neoplasm of the pancreatic gland |
| 32 | Benign endocrine disorders of the pancreas |
| 33 | Malignant neoplasm of the pituitary gland |
| 34 | Benign neoplasm of the pituitary gland |
| 35 | Hyper-functioning adrenal gland |
| 36 | Hypo-functioning adrenal gland |
| 37 | Malignant neoplasm of the adrenal gland |
| 38 | Benign neoplasm of the adrenal gland |
| 39 | Hyper-functioning parathyroid gland |
| 40 | Hypo-functioning parathyroid gland |
| 41 | Malignant neoplasm of the parathyroid gland |
| 42 | Benign neoplasm of the parathyroid gland |
| 43 | Female sex gland disorders |
| 44 | Male sex gland disorders |
| 45 | Nutritional deficiency |

TABLE 1-continued

| ETG | DESCRIPTION |
|---|---|
| 46 | Gout |
| 47 | Metabolic deficiency except gout |
| 48 | Other diseases of the endocrine glands or metabolic disorders, with surgery |
| 49 | Other diseases of the endocrine glands or metabolic disorders, w/o surgery |
| 50 | Endocrine disease signs & symptoms |
| 70 | Leukemia with bone marrow transplant |
| 71 | Leukemia with splenectomy |
| 72 | Leukemia w/o splenectomy |
| 73 | Neoplastic disease of blood and lymphatic system except leukemia |
| 74 | Non-neoplastic blood disease with splenectomy |
| 75 | Non-neoplastic blood disease, major |
| 76 | Non-neoplastic blood disease, minor |
| 77 | Hematology signs & symptoms |
| 90 | Senile or pre-senile mental condition |
| 91 | Organic drug or metabolic disorders |
| 92 | Autism and childhood psychosis |
| 93 | Inorganic psychoses except infantile autism |
| 94 | Neuropsychological & behavioral disorders |
| 95 | Personality disorder |
| 96 | Mental disease signs & symptoms |
| 110 | Cocaine or amphetamine dependence with complications age less than 16 |
| 111 | Cocaine or amphetamine dependence with complications age 16+ |
| 112 | Cocaine or amphetamine dependence w/o complications age less than 16 |
| 113 | Cocaine or amphetamine dependence w/o complications age 16+ |
| 114 | Alcohol dependence with complications, age less than 16 |
| 115 | Alcohol dependence with complications, age 16+ |
| 116 | Alcohol dependence w/o complications, age less than 16 |
| 117 | Alcohol dependence w/o complications, age 16+ |
| 118 | Opioid and/or barbiturate dependence, age less than 16 |
| 119 | Opioid and/or barbiturate dependence, age 16+ |
| 120 | Other drug dependence, age less than 16 |
| 121 | Other drug dependence, age 16+ |
| 140 | Viral meningitis |
| 141 | Bacterial and fungal meningitis |
| 142 | Viral encephalitis |
| 143 | Non-viral encephalitis |
| 144 | Parasitic encephalitis |
| 145 | Toxic encephalitis |
| 146 | Brain abscess, with surgery |
| 147 | Brain abscess, w/o surgery |
| 148 | Spinal abscess |
| 149 | Inflammation of the central nervous system, with surgery |
| 150 | Inflammation of the central nervous system, w/o surgery |
| 151 | Epilepsy, with surgery |
| 152 | Epilepsy, w/o surgery |
| 153 | Malignant neoplasm of the central nervous system, with surgery |
| 154 | Malignant neoplasm of the central nervous system, w/o surgery |
| 155 | Benign neoplasm of the central nervous system, with surgery |
| 156 | Benign neoplasm of the central nervous system, w/o surgery |
| 157 | Cerebral vascular accident, hemorrhagic, with surgery |
| 158 | Cerebral vascular accident, hemorrhagic, w/o surgery |
| 159 | Cerebral vascular accident, non-hemorrhagic, with surgery |
| 160 | Cerebral vascular accident, non-hemorrhagic, w/o surgery |
| 161 | Major brain trauma, with surgery |
| 162 | Major brain trauma, w/o surgery |
| 163 | Minor brain trauma |
| 164 | Spinal trauma, with surgery |
| 165 | Spinal trauma, w/o surgery |
| 166 | Hereditary and degenerative diseases of the central nervous system, with surgery |
| 167 | Hereditary and degenerative diseases of the central nervous system, w/o surgery |
| 168 | Migraine headache, non-intractable |
| 169 | Migraine headache, intractable |
| 170 | Congenital and other disorders of the central nervous system, with surgery |
| 171 | Congenital and other disorders of the central nervous system, w/o surgery |
| 172 | Inflammation of the cranial nerves, with surgery |
| 173 | Inflammation of the cranial nerves, w/o surgery |
| 174 | Carpal tunnel syndrome, with surgery |
| 175 | Carpal tunnel syndrome, w/o surgery |
| 176 | Inflammation of the non-cranial nerves, except carpal tunnel, with surgery |
| 177 | Inflammation of the non-cranial nerves, except carpal tunnel, w/o surgery |
| 178 | Peripheral nerve neoplasm, with surgery |
| 179 | Peripheral nerve neoplasm, w/o surgery |
| 180 | Traumatic disorder of the cranial nerves, with surgery |
| 181 | Traumatic disorder of the cranial nerves, w/o surgery |
| 182 | Traumatic disorder of the non-cranial nerves, with surgery |
| 183 | Traumatic disorder of the non-cranial nerves, w/o surgery |
| 184 | Congenital disorders of the peripheral nerves |

TABLE 1-continued

| ETG | DESCRIPTION |
|---|---|
| 185 | Neurological disease signs & symptoms |
| 200 | Internal eye infection with surgery |
| 201 | Internal eye infection w/o surgery |
| 202 | External eye infection, with surgery |
| 203 | External eye infection, except conjunctivitis, w/o surgery |
| 204 | Conjunctivitis |
| 205 | Inflammatory eye disease, with surgery |
| 206 | Inflammatory eye disease, w/o surgery |
| 207 | Malignant neoplasm of the eye, internal, with surgery |
| 208 | Malignant neoplasm of the eye, internal, w/o surgery |
| 209 | Malignant neoplasm of the eye, external |
| 210 | Benign neoplasm of the eye, internal |
| 211 | Benign neoplasm of the eye, external |
| 212 | Glaucoma, closed angle with surgery |
| 213 | Glaucoma, closed angle w/o surgery |
| 214 | Glaucoma, open angle, with surgery |
| 215 | Glaucoma, open angle, w/o surgery |
| 216 | Cataract, with surgery |
| 217 | Cataract, w/o surgery |
| 218 | Trauma of the eye, with surgery |
| 219 | Trauma of the eye, w/o surgery |
| 220 | Congenital anomaly of the eye, with surgery |
| 221 | Congenital anomaly of the eye, w/o surgery |
| 222 | Diabetic retinopathy, with surgery |
| 223 | Diabetic retinopathy, w/o surgery with comorbidity |
| 224 | Diabetic retinopathy, w/o surgery w/o comorbidity |
| 225 | Non-diabetic vascular retinopathy, with surgery |
| 226 | Non-diabetic vascular retinopathy, w/o surgery |
| 227 | Other vascular disorders of the eye except retinopathies, with surgery |
| 228 | Other vascular disorders of the eye except retinopathies, w/o surgery |
| 229 | Macular degeneration, with surgery |
| 230 | Macular degeneration, w/o surgery |
| 231 | Non-macular degeneration, with surgery |
| 232 | Non-macular degeneration, w/o surgery |
| 233 | Major visual disturbances, with surgery |
| 234 | Major visual disturbances, w/o surgery |
| 235 | Minor visual disturbances, with surgery |
| 236 | Minor visual disturbances, w/o surgery |
| 237 | Other diseases and disorders of the eye and adnexa |
| 250 | Heart transplant |
| 251 | AMI, with coronary artery bypass graft |
| 252 | AMI or acquired defect, with valvular procedure |
| 253 | AMI, with angioplasty |
| 254 | AMI with arrhythmia, with pacemaker implant |
| 255 | AMI, with cardiac catheterization |
| 256 | AMI, anterior wall with complication |
| 257 | AMI, anterior wall w/o complication |
| 258 | AMI, inferior wall with complication |
| 259 | AMI, inferior wall w/o complication |
| 260 | Ischemic heart disease, w/o AMI, with coronary artery bypass graft |
| 261 | Ischemic heart disease, w/o AMI, with valvular procedure |
| 262 | Ischemic heart disease, w/o AMI, with angioplasty |
| 263 | Ischemic heart disease, w/o AMI, with arrhythmia, with pacemaker implant |
| 264 | Ischemic heart disease, w/o AMI, with cardiac catheterization |
| 265 | Ischemic heart disease, w/o AMI |
| 266 | Pulmonary heart disease, w/o AMI |
| 267 | Aortic aneurysm, with surgery |
| 268 | Aortic aneurysm, w/o surgery |
| 269 | Cardiac infection, with surgery |
| 270 | Cardiac infection, w/o surgery |
| 271 | Valvular disorder, with complication |
| 272 | Valvular disorder, w/o complication |
| 273 | Major conduction disorder, with pacemaker/defibrillator implant |
| 274 | Major conduction disorder, w/o pacemaker/defibrillator implant |
| 275 | Minor conduction disorder |
| 276 | Malignant hypertension with comorbidity |
| 277 | Malignant hypertension w/o comorbidity |
| 278 | Benign hypertension with comorbidity |
| 279 | Benign hypertension w/o comorbidity |
| 280 | Cardiac congenital disorder, with surgery |
| 281 | Cardiac congenital disorder, w/o surgery |
| 282 | Major cardiac trauma, with surgery |
| 283 | Major cardiac trauma, w/o surgery |
| 284 | Minor cardiac trauma |
| 285 | Other cardiac diseases |
| 286 | Arterial inflammation, with surgery |
| 287 | Major arterial inflammation, w/o surgery |

TABLE 1-continued

| ETG | DESCRIPTION |
|---|---|
| 288 | Minor arterial inflammation, w/o surgery |
| 289 | Major non-inflammatory arterial disease with surgery |
| 290 | Arterial embolism/thrombosis, w/o surgery |
| 291 | Major non-inflammatory arterial disease, except embolism/thrombosis, w/o surgery |
| 292 | Atherosclerosis, with surgery |
| 293 | Atherosclerosis, w/o surgery |
| 294 | Arterial aneurysm, except aorta, with surgery |
| 295 | Arterial aneurysm, except aorta, w/o surgery |
| 296 | Other minor non-inflammatory arterial disease, with surgery |
| 297 | Other minor non-inflammatory arterial disease, w/o surgery |
| 298 | Arterial trauma, with surgery |
| 299 | Arterial trauma, w/o surgery |
| 300 | Vein inflammation, with surgery |
| 301 | Embolism and thrombosis of the veins |
| 302 | Disorder of the lymphatic channels |
| 303 | Phlebitis and thrombophlebitis of the veins |
| 304 | Varicose veins of the lower extremity |
| 305 | Other minor inflammatory disease of the veins |
| 306 | Venous trauma, with surgery |
| 307 | Venous trauma, w/o surgery |
| 308 | Other diseases of the veins |
| 309 | Cardiovascular disease signs & symptoms |
| 320 | Infection of the oral cavity |
| 321 | Inflammation of the oral cavity, with surgery |
| 322 | Inflammation of the oral cavity, w/o surgery |
| 323 | Trauma of the oral cavity, with surgery |
| 324 | Trauma of the oral cavity, w/o surgery |
| 325 | Other diseases of the oral cavity, with surgery |
| 326 | Other diseases of the oral cavity, w/o surgery |
| 327 | Otitis media, with major surgery |
| 328 | Otitis media, with minor surgery |
| 329 | Otitis media, w/o surgery |
| 330 | Tonsillitis, adenoiditis or pharyngitis, with surgery |
| 331 | Tonsillitis, adenoiditis or pharyngitis, w/o surgery |
| 332 | Sinusitis and Rhinitis, with surgery |
| 333 | Sinusitis and Rhinitis, w/o surgery |
| 334 | Other ENT infection, with surgery |
| 335 | Other ENT infection, w/o surgery |
| 336 | Major ENT inflammatory conditions with surgery |
| 337 | Major ENT inflammatory conditions w/o surgery |
| 338 | Minor ENT inflammatory conditions with surgery |
| 339 | Minor ENT inflammatory conditions w/o surgery |
| 340 | ENT malignant neoplasm, with surgery |
| 341 | ENT malignant neoplasm, w/o surgery |
| 342 | ENT benign neoplasm, with surgery |
| 343 | ENT benign neoplasm, w/o surgery |
| 344 | ENT congenital anomalies, with surgery |
| 345 | ENT congenital anomalies, w/o surgery |
| 346 | Hearing disorders, with surgery |
| 347 | Hearing disorders, w/o surgery |
| 348 | ENT trauma, with surgery |
| 349 | ENT trauma, w/o surgery |
| 350 | Other ENT disorders, with surgery |
| 351 | Other ENT disorders, w/o surgery |
| 352 | Otolaryngology disease signs & symptoms |
| 371 | Viral pneumonia, with comorbidity |
| 372 | Viral pneumonia, w/o comorbidity |
| 373 | Bacterial lung infections, with comorbidity |
| 374 | Bacterial lung infections, w/o comorbidity |
| 375 | Fungal and other pneumonia, with comorbidity |
| 376 | Fungal and other pneumonia, w/o comorbidity |
| 377 | Pulmonary TB with comorbidity |
| 378 | Pulmonary TB w/o comorbidity |
| 379 | Disseminated TB with comorbidity |
| 380 | Disseminated TB w/o comorbidity |
| 381 | Acute bronchitis, with comorbidity, age less than 5 |
| 382 | Acute bronchitis, with comorbidity, age 5+ |
| 383 | Acute bronchitis, w/o comorbidity, age less than 5 |
| 384 | Acute bronchitis, w/o comorbidity, age 5+ |
| 385 | Minor infectious pulmonary disease other than acute bronchitis |
| 386 | Asthma with comorbidity, age less than 18 |
| 387 | Asthma with comorbidity, age 18+ |
| 388 | Asthma w/o comorbidity, age less than 18 |
| 389 | Asthma w/o comorbidity, age 18+ |
| 390 | Chronic bronchitis, with complication with comorbidity |
| 391 | Chronic bronchitis with complication w/o comorbidity |
| 392 | Chronic bronchitis, w/o complication with comorbidity |

TABLE 1-continued

| ETG | DESCRIPTION |
|---|---|
| 393 | Chronic bronchitis w/o complication w/o comorbidity |
| 394 | Emphysema, with comorbidity |
| 395 | Emphysema w/o comorbidity |
| 396 | Occupational and environmental pulmonary diseases, with comorbidity |
| 397 | Occupational and environmental pulmonary diseases, w/o comorbidity |
| 398 | Other inflammatory lung disease, with surgery |
| 399 | Other inflammatory lung disease, w/o surgery |
| 400 | Malignant pulmonary neoplasm, with surgery |
| 401 | Malignant pulmonary neoplasm, w/o surgery |
| 402 | Benign pulmonary neoplasm, with surgery |
| 403 | Benign pulmonary neoplasm, w/o surgery |
| 404 | Chest trauma, with surgery |
| 405 | Chest trauma, open, w/o surgery |
| 406 | Chest trauma, closed, w/o surgery |
| 407 | Pulmonary congenital anomalies, with surgery |
| 408 | Pulmonary congenital anomalies, w/o surgery |
| 409 | Other pulmonary disorders |
| 410 | Pulmonology disease signs & symptoms |
| 430 | Infection of the stomach and esophagus with comorbidity |
| 431 | Infection of the stomach and esophagus w/o comorbidity |
| 432 | Inflammation of the esophagus, with surgery |
| 433 | Inflammation of the esophagus, w/o surgery |
| 434 | Gastritis and/or duodenitis, complicated |
| 435 | Gastritis and/or duodenitis, simple |
| 436 | Ulcer, complicated with surgery |
| 437 | Ulcer, complicated w/o surgery |
| 438 | Ulcer, simple |
| 439 | Malignant neoplasm of the stomach and esophagus, with surgery |
| 440 | Malignant neoplasm of the stomach and esophagus, w/o surgery |
| 441 | Benign neoplasm of the stomach and esophagus, with surgery |
| 442 | Benign neoplasm of the stomach and esophagus, w/o surgery |
| 443 | Trauma or anomaly of the stomach or esophagus, with surgery |
| 444 | Trauma of the stomach or esophagus, w/o surgery |
| 445 | Anomaly of the stomach or esophagus, w/o surgery |
| 446 | Appendicitis, with rupture |
| 447 | Appendicitis, w/o rupture |
| 448 | Diverticulitis, with surgery |
| 449 | Diverticulitis, w/o surgery |
| 450 | Other infectious diseases of the intestines and abdomen |
| 451 | Inflammation of the intestines and abdomen with surgery |
| 452 | Inflammation of the intestines and abdomen, w/o surgery |
| 453 | Malignant neoplasm of the intestines and abdomen, with surgery |
| 454 | Malignant neoplasm of the intestines and abdomen, w/o surgery |
| 455 | Benign neoplasm of the intestines and abdomen, with surgery |
| 456 | Benign neoplasm of the intestines and abdomen, w/o surgery |
| 457 | Trauma of the intestines and abdomen, with surgery |
| 458 | Trauma of the intestines and abdomen, w/o surgery |
| 459 | Congenital anomalies of the intestines and abdomen, with surgery |
| 460 | Congenital anomalies of the intestines and abdomen, w/o surgery |
| 461 | Vascular disease of the intestines and abdomen |
| 462 | Bowel obstruction with surgery |
| 463 | Bowel obstruction w/o surgery |
| 464 | Irritable bowel syndrome |
| 465 | Hernias, except hiatal, with surgery |
| 466 | Hernias, except hiatal, w/o surgery |
| 467 | Hiatal hernia, with surgery |
| 468 | Hiatal hernia, w/o surgery |
| 469 | Other diseases of the intestines and abdomen |
| 470 | Infection of the rectum or anus, with surgery |
| 471 | Infection of the rectum or anus, w/o surgery |
| 472 | Hemorrhoids, complicated, with surgery |
| 473 | Hemorrhoids, complicated, w/o surgery |
| 474 | Hemorrhoids, simple |
| 475 | Inflammation of the rectum or anus, with surgery |
| 476 | Inflammation of the rectum or anus, w/o surgery |
| 477 | Malignant neoplasm of the rectum or anus, with surgery |
| 478 | Malignant neoplasm of the rectum or anus, w/o surgery |
| 479 | Benign neoplasm of the rectum or anus, with surgery |
| 480 | Benign neoplasm of the rectum or anus. w/o surgery |
| 481 | Trauma of the rectum or anus, open, with surgery |
| 482 | Trauma of the rectum or anus, open, w/o surgery |
| 483 | Trauma of the rectum or anus, closed |
| 484 | Other diseases and disorders of the rectum and anus, with surgery |
| 485 | Other diseases and disorders of the rectum and anus, w/o surgery |
| 486 | Gastroenterology disease signs & symptoms |
| 510 | Liver Transplant |
| 511 | Infectious hepatitis, high severity with comorbidity |

TABLE 1-continued

| ETG | DESCRIPTION |
|---|---|
| 512 | Infectious hepatitis, high severity w/o comorbidity |
| 513 | Infectious hepatitis, low severity with comorbidity |
| 514 | Infectious hepatitis, low severity w/o comorbidity |
| 515 | Non-infectious hepatitis, with complications |
| 516 | Non-infectious hepatitis, w/o complications |
| 517 | Cirrhosis, with surgery |
| 518 | Cirrhosis, w/o surgery |
| 519 | Acute pancreatitis |
| 520 | Chronic pancreatitis |
| 521 | Cholelithiasis, complicated |
| 522 | Cholelithiasis, simple, with surgery |
| 523 | Cholelithiasis, simple, w/o surgery |
| 524 | Malignant neoplasm of the hepato-biliary system, with surgery |
| 525 | Malignant neoplasm of the hepato-biliary system, w/o surgery |
| 526 | Benign neoplasm of the hepato-biliary system, with surgery |
| 527 | Benign neoplasm of the hepato-biliary system, w/o surgery |
| 528 | Trauma of the hepato-biliary system, complicated, with surgery |
| 529 | Trauma of the hepato-biliary system, complicated, w/o surgery |
| 530 | Trauma of the hepato-biliary system, simple |
| 531 | Other diseases of the hepato-biliary system, with surgery |
| 532 | Other diseases of the hepato-biliary system, w/o surgery |
| 533 | Hepatology disease signs & symptoms |
| 550 | Kidney Transplant |
| 551 | Acute renal failure, with comorbidity |
| 552 | Acute renal failure, w/o comorbidity |
| 553 | Chronic renal failure, with ESRD |
| 554 | Chronic renal failure, w/o ESRD |
| 555 | Acute renal inflammation, with comorbidity |
| 556 | Acute renal inflammation, w/o comorbidity |
| 557 | Chronic renal inflammation, with surgery |
| 558 | Chronic renal inflammation, w/o surgery |
| 559 | Nephrotic syndrome, minimal change |
| 560 | Nephrotic syndrome |
| 561 | Other renal conditions |
| 562 | Nephrology disease signs & symptoms |
| 570 | Infection of the genitourinary system with surgery |
| 571 | Infection of the genitourinary system w/o surgery |
| 572 | Sexually transmitted infection of the lower genitourinary system |
| 573 | Infection of the lower genitourinary system, not sexually transmitted |
| 574 | Kidney stones, with surgery with comorbidity |
| 575 | Kidney stones, with surgery w/o comorbidity |
| 576 | Kidney stones, w/o surgery with comorbidity |
| 577 | Kidney stones, w/o surgery w/o comorbidity |
| 578 | Inflammation of the genitourinary tract except kidney stones, with surgery |
| 579 | Inflammation of the genitourinary tract except kidney stones, w/o surgery |
| 580 | Malignant neoplasm of the prostate, with surgery |
| 581 | Malignant neoplasm of the prostate, w/o surgery |
| 582 | Benign neoplasm of the prostate, with surgery |
| 583 | Benign neoplasm of the prostate, w/o surgery |
| 584 | Malignant neoplasm of the genitourinary tract, except prostate, with surgery |
| 585 | Malignant neoplasm of the genitourinary tract, except prostate, w/o surgery |
| 586 | Benign neoplasm of the genitourinary tract, except prostate with surgery |
| 587 | Benign neoplasm of the genitourinary tract, except prostate, w/o surgery |
| 588 | Trauma to the genitourinary tract, with surgery |
| 589 | Trauma to the genitourinary tract, w/o surgery |
| 590 | Urinary incontinence, with surgery |
| 591 | Urinary incontinence, w/o surgery |
| 592 | Other diseases of the genitourinary tract, with surgery |
| 593 | Other diseases of the genitourinary tract, w/o surgery |
| 594 | Urological disease signs & symptoms |
| 610 | Normal pregnancy, normal labor & delivery, with cesarean section |
| 611 | Normal pregnancy, normal labor & delivery, w/o cesarean section |
| 612 | Complicated pregnancy, with cesarean section |
| 613 | Complicated pregnancy, w/o cesarean section |
| 614 | Hemorrhage during pregnancy, with cesarean section |
| 615 | Hemorrhage during pregnancy, w/o cesarean section |
| 616 | Other condition during pregnancy, with cesarean section |
| 617 | Other condition during pregnancy, w/o cesarean section |
| 618 | Fetal problems during pregnancy, with cesarean section |
| 619 | Fetal problems during pregnancy, w/o cesarean section |
| 620 | Ectopic pregnancy, with surgery |
| 621 | Ectopic pregnancy, w/o surgery |
| 622 | Spontaneous abortion |
| 623 | Non-spontaneous abortion |
| 624 | Obstetric signs & symptoms |
| 630 | Infection of the ovary and/or fallopian tube, with surgery |
| 631 | Infection of the ovary and/or fallopian tube, w/o surgery, with comorbidity |

TABLE 1-continued

| ETG | DESCRIPTION |
|---|---|
| 632 | Infection of the ovary and/or fallopian tube, w/o surgery, w/o comorbidity |
| 633 | Infection of the uterus, with surgery |
| 634 | Infection of the uterus, w/o surgery, with comorbidity |
| 635 | Infection of the uterus, w/o surgery, w/o comorbidity |
| 636 | Infection of the cervix, with surgery |
| 637 | Infection of the cervix, w/o surgery |
| 638 | Vaginal infection, with surgery |
| 639 | Monilial infection of the vagina (yeast) |
| 640 | Infection of the vagina except monilial |
| 641 | Inflammation of the female genital system, with surgery |
| 642 | Endometriosis, w/o surgery |
| 643 | Inflammatory condition of the female genital tract except endometriosis, w/o surgery |
| 644 | Malignant neoplasm of the female genital tract, with surgery |
| 645 | Malignant neoplasm of the female genital tract, w/o surgery |
| 646 | Benign neoplasm of the female genital tract, with surgery |
| 647 | Benign neoplasm of the female genital tract, w/o surgery |
| 648 | Conditions associated with menstruation, with surgery |
| 649 | Conditions associated with menstruation, w/o surgery |
| 650 | Conditions associated with female infertility, with surgery |
| 651 | Conditions associated with female infertility, w/o surgery |
| 652 | Other diseases of the female genital tract, with surgery |
| 653 | Other diseases of the female genital tract, w/o surgery |
| 654 | Malignant neoplasm of the breast, with surgery |
| 655 | Malignant neoplasm of the breast, w/o surgery |
| 656 | Benign neoplasm of the breast, with surgery |
| 657 | Benign neoplasm of the breast, w/o surgery |
| 658 | Other disorders of the breast, with surgery |
| 659 | Other disorders of the breast, w/o surgery |
| 660 | Gynecological signs & symptoms |
| 670 | Major bacterial infection of the skin, with surgery |
| 671 | Major bacterial infection of the skin, w/o surgery |
| 672 | Minor bacterial infection of the skin |
| 673 | Viral skin infection |
| 674 | Fungal skin infection, with surgery |
| 675 | Fungal skin infection, w/o surgery |
| 676 | Parasitic skin infection |
| 677 | Major inflammation of skin & subcutaneous tissue |
| 678 | Minor inflammation of skin & subcutaneous tissue |
| 679 | Malignant neoplasm of the skin, major, with surgery |
| 680 | Malignant neoplasm of the skin, major, w/o surgery |
| 681 | Malignant neoplasm of the skin, minor |
| 682 | Benign neoplasm of the skin |
| 683 | Major burns, with surgery |
| 684 | Major burns, w/o surgery |
| 685 | Major skin trauma, except burns, with surgery |
| 686 | Major skin trauma, except burns, w/o surgery |
| 687 | Minor burn |
| 688 | Minor trauma of the skin except burn, with surgery |
| 689 | Open wound of the skin, w/o surgery |
| 690 | Minor trauma of the skin except burn and open wound, w/o surgery |
| 691 | Other skin disorders |
| 692 | Dermatological signs & symptoms |
| 710 | Infection of the large joints with comorbidity |
| 711 | Infection of the large joints w/o comorbidity |
| 712 | Infection of the small joints with comorbidity |
| 713 | Infection of the small joints w/o comorbidity |
| 714 | Degenerative orthopedic diseases with hip or spine surgery |
| 715 | Degenerative orthopedic diseases with large joint surgery |
| 716 | Degenerative orthopedic diseases with hand or foot surgery |
| 717 | Juvenile rheumatoid arthritis with complication with comorbidity |
| 718 | Juvenile rheumatoid arthritis with complication w/o comorbidity |
| 719 | Juvenile rheumatoid arthritis w/o complication with comorbidity |
| 720 | Juvenile rheumatoid arthritis w/o complication w/o comorbidity |
| 721 | Adult rheumatoid arthritis with complication with comorbidity |
| 722 | Adult rheumatoid arthritis with complication w/o comorbidity |
| 723 | Adult rheumatoid arthritis w/o complication with comorbidity |
| 724 | Adult rheumatoid arthritis w/o complication w/o comorbidity |
| 725 | Lupus, with complication |
| 726 | Lupus, w/o complication |
| 727 | Autoimmune rheumatologic disease except lupus |
| 728 | Inflammation of the joints other than rheumatoid arthritis, with comorbidity |
| 729 | Inflammation of the joints other than rheumatoid arthritis, w/o comorbidity |
| 730 | Degenerative joint disease, generalized |
| 731 | Degenerative joint disease, localized with comorbidity |
| 732 | Degenerative joint disease, localized w/o comorbidity |
| 733 | Infections of bone, with surgery |
| 734 | Infections of bone, w/o surgery |

TABLE 1-continued

| ETG | DESCRIPTION |
|---|---|
| 735 | Maxillofacial fracture or dislocation, with surgery |
| 736 | Maxillofacial fracture or dislocation, w/o surgery |
| 737 | Pelvis fracture or dislocation, with surgery |
| 738 | Pelvis fracture or dislocation, w/o surgery |
| 739 | Hip and/or femur fracture or dislocation, with surgery |
| 740 | Hip and/or femur fracture or dislocation, open, w/o surgery |
| 741 | Hip and/or femur fracture or dislocation, closed, w/o surgery |
| 742 | Upper extremity fracture or dislocation, with surgery |
| 743 | Upper extremity fracture or dislocation, open, w/o surgery |
| 744 | Upper extremity fracture or dislocation, closed, w/o surgery |
| 745 | Lower extremity fracture or dislocation, with surgery |
| 746 | Lower extremity fracture or dislocation, open, w/o surgery |
| 747 | Lower extremity fracture or dislocation, closed, w/o surgery |
| 748 | Trunk fracture or dislocation, with surgery |
| 749 | Trunk fracture or dislocation, open, w/o surgery |
| 750 | Trunk fracture or dislocation, closed, w/o surgery |
| 751 | Malignant neoplasm of the bone and connective tissue, head and neck |
| 752 | Malignant neoplasm of the bone and connective tissue other than head and neck |
| 753 | Benign neoplasm of the bone and connective tissue, head and neck |
| 754 | Benign neoplasm of the bone and connective tissue other than head and neck |
| 755 | Internal derangement of joints, with surgery |
| 756 | Internal derangement of joints, w/o surgery |
| 757 | Major orthopedic trauma other than fracture or dislocation, with surgery |
| 758 | Major orthopedic trauma other than fracture or dislocation, w/o surgery |
| 759 | Major neck and back disorders, with surgery |
| 760 | Major neck and back disorders, w/o surgery |
| 761 | Bursitis and tendinitis, with surgery |
| 762 | Bursitis and tendinitis, w/o surgery |
| 763 | Minor orthopedic disorder except bursitis and tendinitis, with surgery |
| 764 | Minor neck and back disorder, except bursitis and tendinitis, w/o surgery |
| 765 | Minor orthopedic disorder other than neck and back, except bursitis and tendinitis, w/o surgery |
| 766 | Orthopedic congenital and acquired deformities, with surgery |
| 767 | Orthopedic congenital and acquired deformities, w/o surgery |
| 768 | Orthopedic and rheumatological signs & symptoms |
| 780 | Uncomplicated neonatal management |
| 781 | Chromosomal anomalies |
| 782 | Metabolic related disorders originating the antenatal period |
| 783 | Chemical dependency related disorders originating in the antenatal period |
| 784 | Mechanical related disorders originating in the antenatal period |
| 785 | Other disorders originating in the antenatal period |
| 786 | Other major neonatal disorders, perinatal origin |
| 787 | Other minor neonatal disorders, perinatal origin |
| 788 | Neonatal signs & symptoms |
| 790 | Exposure to infectious diseases |
| 791 | Routine inoculation |
| 792 | Non-routine inoculation |
| 793 | Prophylactic procedures other than inoculation and exposure to infectious disease |
| 794 | Routine exam |
| 795 | Contraceptive management, with surgery |
| 796 | Contraceptive management, w/o surgery |
| 797 | Conditional exam |
| 798 | Major specific procedures not classified elsewhere |
| 799 | Minor specific procedures not classified elsewhere |
| 800 | Administrative services |
| 801 | Other preventative and administrative services |
| 810 | Late effects and late complications |
| 811 | Environmental trauma |
| 812 | Poisonings and toxic effects of drugs |
| 900 | Isolated signs, symptoms and non-specific diagnoses or conditions |
| 990 | Drug record, no drug module |
| 991 | Orphan drug record |
| 992 | Non-Rx NDC code |
| 993 | Invalid NDC code |
| 994 | Invalid provider type, e.g., dentist |
| 995 | Record outside date range |
| 996 | Invalid CPT-4 code |
| 997 | Invalid Dx code |
| 998 | Inappropriate Dx-CPT-4 matched record |
| 999 | Orphan record |

What is claimed is:

1. A computer-implemented method for processing medical claim data records, the medical claim data records each including at least one of a diagnosis, procedure or drug code, comprising one or more computers performing the following:

storing a plurality of diagnostic groups in at least one data storage device, wherein each diagnostic group is associated with one or more diagnosis, procedure or drug codes;

upon receiving a first medical claim data record associated with a patient, processing the first medical claim data record using at least one data processor to: identify one or more diagnosis, procedure or drug codes in the first medical claim data record; compare the identified codes in the first medical claim data record with the codes associated with one or more of the plurality of the stored diagnostic groups; and assign the first medical claim data record to a first diagnostic group based upon the one or more diagnosis, procedure or drug codes identified in the first medical claim data record; and upon receiving a second medical claim data record associated with the patient, processing the second medical claim data record using the data processor to: identify one or more diagnosis, procedure or drug codes in the second medical claim data record; determine whether the identified codes in the second medical claim data record indicate a change in the patient's clinical condition; and, shift the first medical claim data record from the first diagnostic group to a second diagnostic group that includes the change in the patient's clinical condition.

2. The method according to claim 1, wherein the change in the patient's clinical condition indicated by the codes in the second medical claim data record represents a complication, co-morbidity, surgery or changed severity of the clinical condition of the patient.

3. The method of claim 1, wherein upon receiving a third medical claim data record associated with the patient, the third medical claim data record is processed by the data processor to: identify one or more diagnosis, procedure or drug codes in the third medical claim data record; determine whether the identified codes in the third medical claim data record indicate an additional change in the patient's clinical condition; and, if so, shift the first medical claim data record from the second diagnostic group to a third diagnostic group that includes the additional change in the patient's clinical condition.

4. The method of claim 3, wherein the change in the patient's clinical condition indicated by the codes in the third medical claim data record represents a complication, co-morbidity, surgery or changed severity of the clinical condition of the patient.

5. The method of claim 1, wherein the diagnostic groups are episode treatment groups.

* * * * *

UNITED STATES PATENT AND TRADEMARK OFFICE
CERTIFICATE OF CORRECTION

PATENT NO. : 7,774,216 B2  Page 1 of 1
APPLICATION NO. : 11/841439
DATED : August 10, 2010
INVENTOR(S) : Dennis K. Dang It is certified that error appears in the above-identified patent and that said Letters Patent is hereby corrected as shown below:

SPECIFICATION

| Column | Line | PTO | Should Read |
|---|---|---|---|
| 6 | 46 | "change in the patients condition" | --change in the patient's condition-- |
| 16 | 57 | "Bridge 1308" | --Bridge I 308-- |

Signed and Sealed this

Sixteenth Day of November, 2010

David J. Kappos
*Director of the United States Patent and Trademark Office*